(12) United States Patent
Penninger et al.

(10) Patent No.: US 8,124,067 B2
(45) Date of Patent: Feb. 28, 2012

(54) METHOD FOR IMMUNOTHERAPY OF TUMORS

(75) Inventors: Josef Penninger, Vienna (AT); Urs Eriksson, Basel (CH)

(73) Assignee: IMBA-Institute Fur Molekulre Biotechnologie GmbH, Vienna (AT)

( * ) Notice: Subject to any disclaimer, the term of this patent is extended or adjusted under 35 U.S.C. 154(b) by 468 days.

(21) Appl. No.: 10/567,167

(22) PCT Filed: Aug. 4, 2004

(86) PCT No.: PCT/IB2004/002788
§ 371 (c)(1),
(2), (4) Date: Feb. 3, 2006

(87) PCT Pub. No.: WO2005/012509
PCT Pub. Date: Feb. 10, 2005

(65) Prior Publication Data
US 2006/0147427 A1    Jul. 6, 2006

Related U.S. Application Data

(60) Provisional application No. 60/491,988, filed on Aug. 4, 2003.

(51) Int. Cl.
| A01N 63/00 | (2006.01) |
| A61K 49/00 | (2006.01) |
| A61K 39/00 | (2006.01) |
| C12N 5/00 | (2006.01) |
| C12N 5/02 | (2006.01) |
| C12N 15/11 | (2006.01) |
| C12N 15/00 | (2006.01) |
| G01N 33/00 | (2006.01) |
| A01K 67/00 | (2006.01) |

(52) U.S. Cl. .... 424/93.1; 424/9.1; 424/93.7; 424/277.1; 435/325; 435/377; 514/44; 800/3; 800/8; 800/21

(58) Field of Classification Search .................... None
See application file for complete search history.

(56) References Cited

FOREIGN PATENT DOCUMENTS
WO      WO 03/020889      *  3/2003
WO      WO 03/024480         3/2003

OTHER PUBLICATIONS

Kadowaki et al., 2002, Human Immunology 63:1126-1132.*
Turley et al., 2002 Curr. Opin. Immunol. 14:765-770.*
Prummerer et al., 1996, J.Clin. Invest. 97:2057-2062.*
Zhang., 2002, Cancer biotherapy and Radiopharmaceuticals 17:601-619.*
Brawand et al., 2002, J.Immunol 169:6711-6719.*
Krug et al., 2001, Eur.J.Immunol 31:3026-3037.*
Morse at al., 1998, Cancer Res. 58:2965-2968.*
Ludewig et al., 2000, J. Exp. Med. 191:795-803.*
Watanabe et al.,1999, Autoimmunity 31:273-82 (Abstract only p. 1 of 1).*
Weir et al., 2002, Immunol. Cell Biol. 80:14-20 Abstract only p. 1 of 1).*

(Continued)

Primary Examiner — Robert M Kelly
Assistant Examiner — Kelaginamane T Hiriyanna
(74) Attorney, Agent, or Firm — Fulbright & Jaworski LLP

(57) ABSTRACT

A method for making dendritic cells reactive to an antigen comprises obtaining a sample of dendritic cells and contacting the cells with the antigen and at least one Toll-like receptor stimulant. Dendritic cells activated by this method provide a means for treating tumors and for creating animal models of autoimmune diseases.

27 Claims, 9 Drawing Sheets

OTHER PUBLICATIONS

Bachmaier et al., "*Chlamydia* Infections and Heart Disease Linked Through Antigenic Mimicry," *Science*, 283:1335-1339, 1999.

Banchereau and Steinman, "Dendritic cells and the control of immunity," *Nature*, 392:245-252, 1998.

Benoist and Mathis, "Autoimmunity provoked by infection: how good is the case for T cell epitope mimicry?" *Nat. Immunol.*, 2:797-801, 2001.

Caforio et al, "Circulating cardiac autoantibodies in dilated cardiomyopathy and myocarditis: pathogenetic and clinical significance," *Eur. J. Heart Fail.*, 4:411-417, 2002.

Calabrese et al., "Molecular diagnosis of myocarditis and dilated cardiomyopathy in children: clinicopathologic features and prognostic implications," *Diagn. Mol. Pathol.*, 11:212-221, 2002.

Campos et al., "Activation of Toll-like receptor-2 by glycosylphosphatidylinositol anchors from a protozoan parasite," *J. Immunol.*, 167:416-423, 2001.

Cella et al., "Ligation of CD40 on dendritic cells triggers production of high levels of interleukin-12 and enhances T cell stimulatory capacity: T-T help via APC activation," *J. Exp. Med.*, 184:747-752, 1996.

Crackower et al., "Angiotensin-converting enzyme 2 is an essential regulator of heart function," *Nature*, 417:822-828, 2002.

Donermeyer et al., "Myocarditis-inducing epitope of myosin binds constitutively and stably to I-Ak on antigen-presenting cells in the heart," *J. Exp. Med.*, 182:1291-1300, 1995.

Eriksson et al., "Activation of dendritic cells through the interleukin 1 receptor 1 is critical for the induction of autoimmune myocarditis," *J. Exp. Med.*, 197:323-331, 2003.

Eriksson et al., "Dual role of the IL-12/IFN-gamma axis in the development of autoimmune myocarditis: induction by IL-12 and protection by IFN-gamma," *J. Immunol.*, 167:5464-5469, 2001.

Eriksson et al., "Dendritic cell-induced autoimmune heart failure requires cooperation between adaptive and innate immunity," *Nat. Med.*, 9:1484-1490, 2003.

Feldman et al., "Myocarditis," *New England J. Med.*, 343:1388-1398, 2000.

Futagawa et al., "Expression and function of 4-1BB and 4-1BB ligand on murine dendritic cells," *Int. Immunol.*, 14:275-286, 2002.

Grewal et al., "Impairment of antigen-specific T-cell priming in mice lacking CD40 ligand," *Nature*, 378:617-620, 1995.

Howard and Miller, "Autoimmune intervention by CD154 blockade prevents T cell retention and effector function in the target organ," *J. Immunol.*, 166:1547-1553, 2001.

Josien et al., "TRANCE, a tumor necrosis factor family member, enhances the longevity and adjuvant properties of dendritic cells in vivo," *J. Exp. Med.*, 191:495-502, 2000.

Kawabe et al., "The Immune Responses in CD40-Deficient Mice: Impaired Immunoglobulin Class Switching and Germinal Center Formation," *Immunity*, 1:167-178, 1994.

Kong et al., "Activated T cells regulate bone loss and joint destruction in adjuvant arthritis through osteoprotegerin ligand," *Nature*, 402:304-309, 1999.

Krishnagopalan et al., "Myocardial dysfunction in the patient with sepsis," *Curr. Opin. Crit. Care*, 8:376-388, 2002.

Labow et al., "Absence of IL-1 signaling and reduced inflammatory response in IL-1 type I receptor-deficient mice," *J. Immunol.*, 159:2452-2461, 1997.

Libby et al., "Inflammation and Atherosclerosis," *Circulation*, 105:1135-1143, 2002.

Liu et al., "Immune tolerance after delivery of dying cells to dendritic cells in situ," *J. Exp. Med.*, 196:1091-1097, 2002.

Liuzzo et al., "The Prognostic Value of C-Reactive Protein and Serum Amyloid a Protein in Severe Unstable Angina," *New England Journal Med.*, 31: 417-424, 1994.

Ludewig et al., "Dendritic cells induce autoimmune diabetes and maintain disease via de novo formation of local lymphoid tissue," *J. Exp. Med.*, 188:1493-1501, 1998.

Lutz et al., "An advanced culture method for generating large quantities of highly pure dendritic cells from mouse bone marrow," *J. Immunol Methods*, 223:77-92, 1999.

Magram et al., "IL-12-Deficient Mice Are Defective in IFNγ Production and Type 1 Cytokine Responses," *Immunity*, 4:471-478, 1996.

Mann, "Inflammatory mediators and the failing heart: past, present, and the foreseeable future," *Circ. Res.*, 91:988-998, 2002.

Means et al., "Human toll-like receptors mediate cellular activation by *Mycobacterium tuberculosis*," *J. Immunol.*, 163:3920-3927, 1999.

Medzhitov and Janeway, "Decoding the Patterns of Self and Nonself by the Innate Immune System," *Science*, 296:298-300. 2002.

Mellman and Steinman, "Dendritic cells: specialized and regulated antigen processing machines," *Cell*, 106:255-258, 2001.

Menges et al., "Repetitive injections of dendritic cells matured with tumor necrosis factor alpha induce antigen-specific protection of mice from autoimmunity," *J. Exp. Med.*, 195:15-21, 2002.

Neu et al., "Cardiac myosin induces myocarditis in genetically predisposed mice," *J. Immunol.*, 139:3630-3636, 1987.

Nishimura et al., "Autoimmune Dilated Cardiomyopathy in PD-1 Receptor-Deficient Mice," *Science*, 291:319-322, 2001.

Pontes-de-Carvalho et al., "Experimental chronic Chagas' disease myocarditis is an autoimmune disease preventable by induction of immunological tolerance to myocardial antigens," *J. Autoimmun.*, 18:131-138, 2002.

Pulendran et al., "Sensing Pathogens and Tuning Immune Responses," *Science*, 293: 253-256, 2001.

Pummerer et al., "Identification of cardiac myosin peptides capable of inducing autoimmune myocarditis in BALB/c mice," *J. Clin. Invest.*, 97:2057-2062, 1996.

Roig et al., "Serum interleukin-6 in congestive heart failure secondary to idiopathic dilated cardiomyopathy," *Am. J. Cardiol.*, 82:688-690, 1998.

Rose and Bona, "Defining criteria for autoimmune diseases (Witebsky's postulates revisited)," *Immunol. Today*, 14:426-430, 1993.

Rose et al., "Autoimmune myocarditis: a paradigm of post-infection autoimmune disease," *Immunol. Today*, 9:117-120, 1988.

Smith and Allen, "Expression of myosin-class II major histocompatibility complexes in the normal myocardium occurs before induction of autoimmune myocarditis," *Proc. Natl. Acad. Sci. USA*, 89:9131-9135, 1992.

Steinbrink et al., "Induction of tolerance by IL-10-treated dendritic cells," *Journal of Immunology*, 159:4772-4780, 1997.

Steinman and Nussenzweig, "Avoiding horror autotoxicus: The importance of dendritic cells in peripheral T cell tolerance," *Proc. Natl. Acad. Sci. USA*, 99:351-358, 2001.

Turley, "Dendritic cells: inciting and inhibiting autoimmunity," *Curr. Opin. Immunol.*, 14:765-770, 2002.

Weir et al., "Experimental autoimmune encephalomyelitis induction in naive mice by dendritic cells presenting a self-peptide," *Immunology and Cell Biology*, 80:14-20, 2002.

Japanese Office Action, issued in Japanese Patent Application No. 2006-522445, dated Jun. 22, 2010.

Demangel et al., "Stimulation of dentritic cells via CD40 enhances immune responses to *Mycobacterium tuberculosis* infection," *Infection and Immunity*, 69:2456-2461, 2001.

Kawachi, "Mechanism of autoimmunity in human polymyositis, based on the experimental allergic myositis induced by inoculating dendritic cells," *Niigata Medical Journal*, 116:546-565, 2002.

Office Action issued in Japanese Patent Application No. 2006-522445, dated Feb. 15, 2011. (English Translation enclosed).

Takesue et al.,"An Investigation of Possible Activation Stimulation in Respect of CD8-Positive Lymphocytes of the Atypical Peripheral Blood Dendritic Type Cell Sub-Group," 3-D-W19-34-P. 31:265, 2001:(English translation).

* cited by examiner

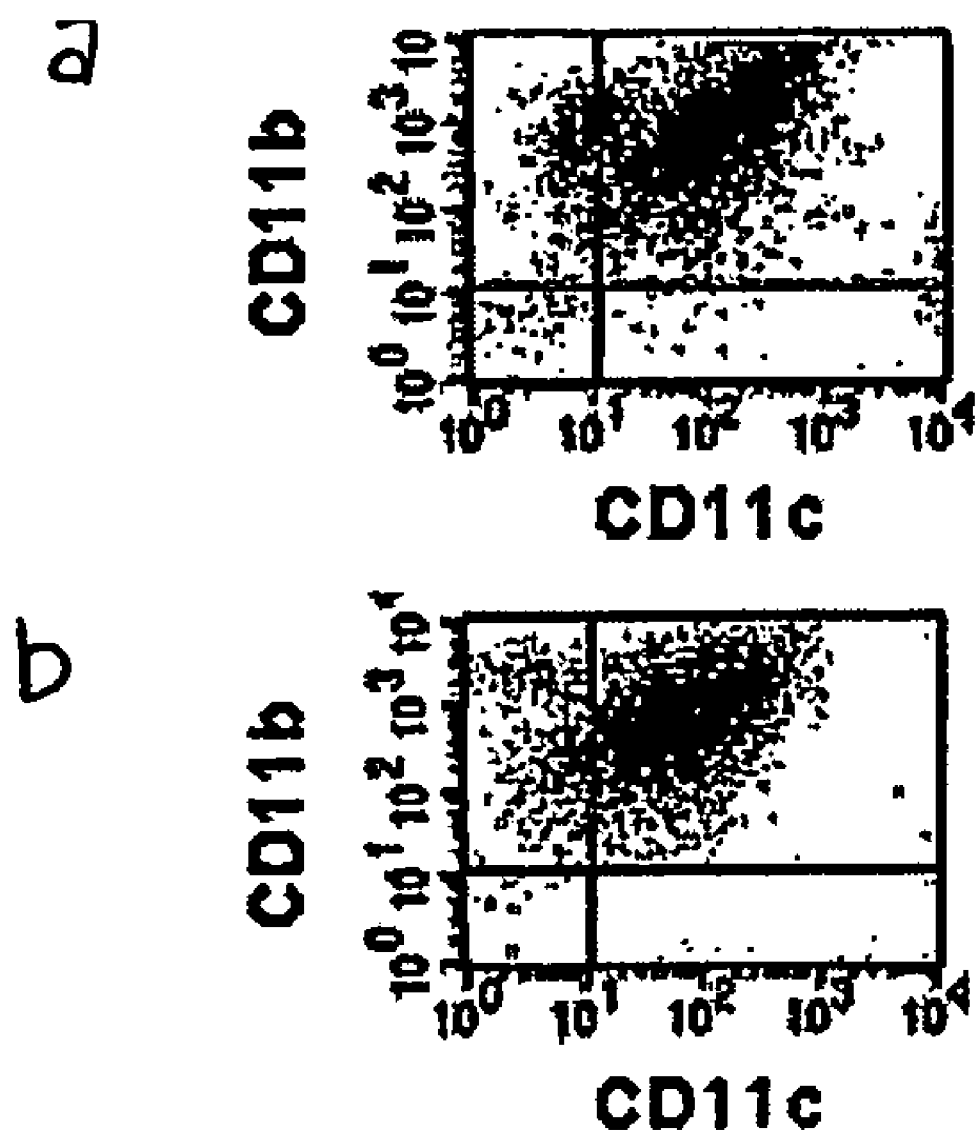
Figure 6A and B

METHOD FOR IMMUNOTHERAPY OF TUMORS

FIELD OF THE INVENTION

This invention relates to a method for the production of reactive dendritic cells and in particular to the use of the reactive dendritic cells for tumor vaccination, to create an animal model of organ failure and for use in in vitro drug screening.

BACKGROUND OF THE INVENTION

Infections and inflammation have now emerged as important risk factors for cardiovascular diseases[1], the major cause of death in Western societies. Indeed, elevation of inflammatory markers in the serum predicts the prognosis of patients with coronary heart diseases[2] and dilated cardiomyopathy[3,4]. In particular, dilated cardiomyopathy, the commonest cause of heart failure in young patients[5,6,7], has been linked to autoimmune responses following infection with cardiotropic viruses, since many of these patients display autoantibodies against heart proteins[6,7,8]. Similar autoimmune mechanisms have been implicated in heart failure after infection with the protozoan Trypanozoma cruzii[7]. Autoimmunity is characterized by a number of classic criteria[24], including defined self-antigens, organ specificity and autoreactive T-cells and/or autoantibodies that can transfer disease.

Animal models support the idea that microbial infection can trigger autoimmune responses against heart tissue[7]. Mice with defined genetic backgrounds develop prolonged myocarditis, with autoreactive T-cells, after Coxsackie B3[7] and Trypanozoma cruzii[9] infection. In the same mouse strains, immunization with heart specific α-myosin or a sixteen amino acid, α-myosin-heavy-chain epitope together with strong adjuvant induces T-cell mediated myocarditis[7,10,11]. Importantly, it has been shown that hearts from normal mice contain large numbers of tissue-resident cells presenting endogenous heart specific peptides[12]. It is not known, however, whether dendritic cells presenting endogenous self-antigens might contribute to autoimmune heart disease and possibly heart failure. What is needed is an animal model that allow researchers to study the mechanisms by which cardiomyopathy develops in young patients and, more importantly, to identify compounds that interfere with that development.

Dendritic cells are key players in the induction of antigen-specific immune responses[13,14,15] as well as of immunotolerance[16,17]. Immature dendritic cells reside in the peripheral tissues, where they actively sample their environment by endocytosis and macropinocytosis. Upon encountering a pathogen, they undergo a developmental program called dendritic cell maturation, which includes induction of costimulatory activity, antigen processing, increased MHC molecule expression, and migration to the lymph node, where they can prime naïve antigen-specific T cells[13]. Dendritic cells also process endogenous antigens from debris and dead cells[13,15,16]. It has therefore been proposed that dendritic cells might trigger autoreactive T-cells if activated appropriately[13,17]. There is increasing evidence that processing of dying cells and self-tissue, in the absence of appropriate stimulation, renders dendritic cells tolerogenic for CD8$^+$ T-cell[18]- and CD4$^+$ T-cell[19]-mediated immune responses. Current research has therefore focused on the role of dendritic cells in maintaining self-tolerance. Some research has indicated that dendritic cells can induce organ-specific inflammation in a transgenic model of viral antigen expression[20], but there is still only indirect evidence that activated dendritic cells can induce autoimmunity to self-antigens[13,21]. Moreover, it has never been shown that dendritic cells pulsed with self-proteins are indeed capable of inducing autoimmunity in "naïve" mice. Dendritic cells express multiple Toll-like receptors and therefore these cells are pivotally positioned at the interface of adaptive and innate immunity[21]. The innate immune system is a universal and ancient form of host defense against infection[21].

Dendritic cells are comprised of a heterogeneous cell population with a widespread tissue distribution. The use of dendritic cells for research and more practical applications has been limited due to the low frequency of dendritic cells in peripheral blood, the limited accessibility of lymphoid organs and the dendritic cells' terminal state of differentiation. The number of dendritic cells necessary for activation by current methods is of the order of at least $1 \times 10^6$ cells. What is needed is a method for dendrite cell activation that requires fewer cells, of the order of $5 \times 10^4$ to $2 \times 10^5$ cells.

Research has shown that the immune system is capable of killing tumor cells to some extent; tumors nevertheless often prevail. Various methods for immunotherapy to treat cancers have been suggested but a therapeutic method that successfully elicits an effective and specific immunotherapeutic response against a target tumor has not yet been realized. What is needed is a method that consistently and specifically generates an immune response to a tumor in vivo, resulting in the eradication of the tumor.

All publications and patent applications referred to herein are fully incorporated by reference to the extent not inconsistent herewith.

SUMMARY OF THE INVENTION

A method is disclosed for activating dendritic cells to become reactive to a selected antigen. In this method, dendritic cells are exposed to the selected antigen and to a stimulant of a Toll-like receptor (TLR), which activates a TLR pathway in the dendritic cells.

Where the selected antigen to which the dendritic cells are exposed is an autoantigen or a tissue specific antigen, reintroduction of the activated dendritic cells into an animal whose tissues carry that antigen leads to the development of autoimmune disease in the animal. This provides a method for creating an animal model of an autoimmune disease or of tissue specific autoimmune damage. Selection of an autoantigen associated with an autoimmune disease allows one to model the autoimmune disease, as described herein.

Where the selected antigen to which the dendritic cells are exposed is a tumor antigen, reintroduction of the activated dendritic cells into the tumor subject provides a novel method of immunotherapy, as described herein.

In accordance with one embodiment of the present invention, there is provided a method for making dendritic cells reactive to an antigen comprising:
   obtaining a sample of dendritic cells; and
   contacting the dendritic cells with the antigen and with at least one Toll-like receptor (TLR) stimulant.

In accordance with another embodiment of the present invention, there is provided a method for treating a tumor in an animal comprising obtaining a tumor antigen expressed by the tumor, obtaining a sample of dendritic cells from the animal, making the dendritic cells reactive to the tumor antigen by the method described above and reintroducing the reactive dendritic cells into the animal.

In accordance with a further embodiment of the present invention, there is provided a method of making an animal model of an autoimmune disease comprising obtaining an antigen associated with the autoimmune disease, obtaining a sample of dendritic cells from a non-human animal, making the dendritic cells reactive to the antigen associated with the autoimmune disease by the method described above and reintroducing the reactive dendritic cells into the animal.

In accordance with another embodiment of the present invention, there is provided a method of making an animal model of organ failure comprising obtaining an organ-specific autoantigen, obtaining a sample of dendritic cells from a non-human animal, making the dendritic cells reactive to the autoantigen by the method described above and reintroducing the reactive dendritic cells into the animal.

In accordance with a further embodiment of the present invention, there is provided the method as described above wherein the antigen is myhc-α peptide.

In accordance with another embodiment of the present invention, there is provided a method for screening a candidate compound for its ability to modulate the development of an autoimmune disease in an animal comprising obtaining an autoantigen associated with the autoimmune disease, obtaining a sample of dendritic cells from a non-human animal, making the dendritic cells reactive to the autoantigen by the method of any one of claims 1 to 12 and reintroducing the reactive dendritic cells into the animal, wherein the dendritic cells are contacted with the candidate compound at a time selected from prior to contact with the autoantigen, during contact with the autoantigen, after contact with the autoantigen and prior to contact with the TLR stimulant, during contact with the TLR stimulant and after contact with the TLR stimulant, and comparing the autoimmune reaction in the animal with the autoimmune reaction in an animal treated with dendritic cells made reactive to the same autoantigen and not exposed to the compound.

SUMMARY OF THE DRAWINGS

The present invention will be further understood from the following detailed description of certain embodiments of the invention, with reference to the drawings in which:

FIG. 3a shows heart to body weight ratios, FIG. 3b shows left ventricular end diastolic diameter (LVEDD), FIG. 3c shows echocardiograms from control and test mice. FIG. 3d shows the velocity of circumferential fiber shortening (VCFC) and FIG. 3e shows fractional shortening (FC).

FIGS. 4a and 4d show heart tissue when CD40$^{-/-}$ dendritic cells are inoculated into CD40$^{+/+}$ hosts. FIGS. 4b and 4e show heart tissue when CD40$^{+/+}$ dendritic cells are inoculated into CD40$^{-/-}$ hosts. FIGS. 4c and 4f show heart tissue when CD40$^{+/+}$ dendritic cells are inoculated into CD40$^{+/+}$ hosts.

FIGS. 6a, 6b and 6c show the expression of costimulatory molecules on CD40$^{+/+}$ (blue) and CD40$^{-/-}$ (red) dendritic cells after stimulation with LPS/anti-CD40 for 12 hours. FACS histograms were gated on CD11c+ CD11b+ MHC class II+ live cells (ICAM, B7.1, B7.2) or CD11c+ CD11b+ live cells.

FIG. 8b shows the heart tissue of control mice injected with 2×10$^6$ apoptotic cardiomyocytes (i.p.) without LPS does not induce myocarditis (0 of 6 mice). FIG. 8c shows the heart tissue of mice injected with 2×10$^6$ apoptotic cardiomyocytes (i.p.) together with LPS (10 µg i.p. on day 0,1,2) resulted in cardiac inflammation (arrow) in 7 out of 8 mice. Of note, inoculation of LPS alone did not induce heart inflammation (0 of 5 mice; not shown). p<0.0001 for LPS/cardiomyocytes vs. cardiomyocytes (Fisher's exact test). FIG. 8d shows anti-myhc-α IgG autoantibody titers 10 days after i.p. inoculation of LPS and 2×10$^6$ apoptotic cardiomyocytes (LPS) or the control of just apoptotic cardiomyocytes. Inoculation of cardiomyocytes alone did not induce relevant antibody titers (Control). Data from individual mice are shown.

DESCRIPTION OF THE INVENTION

Figure 1:
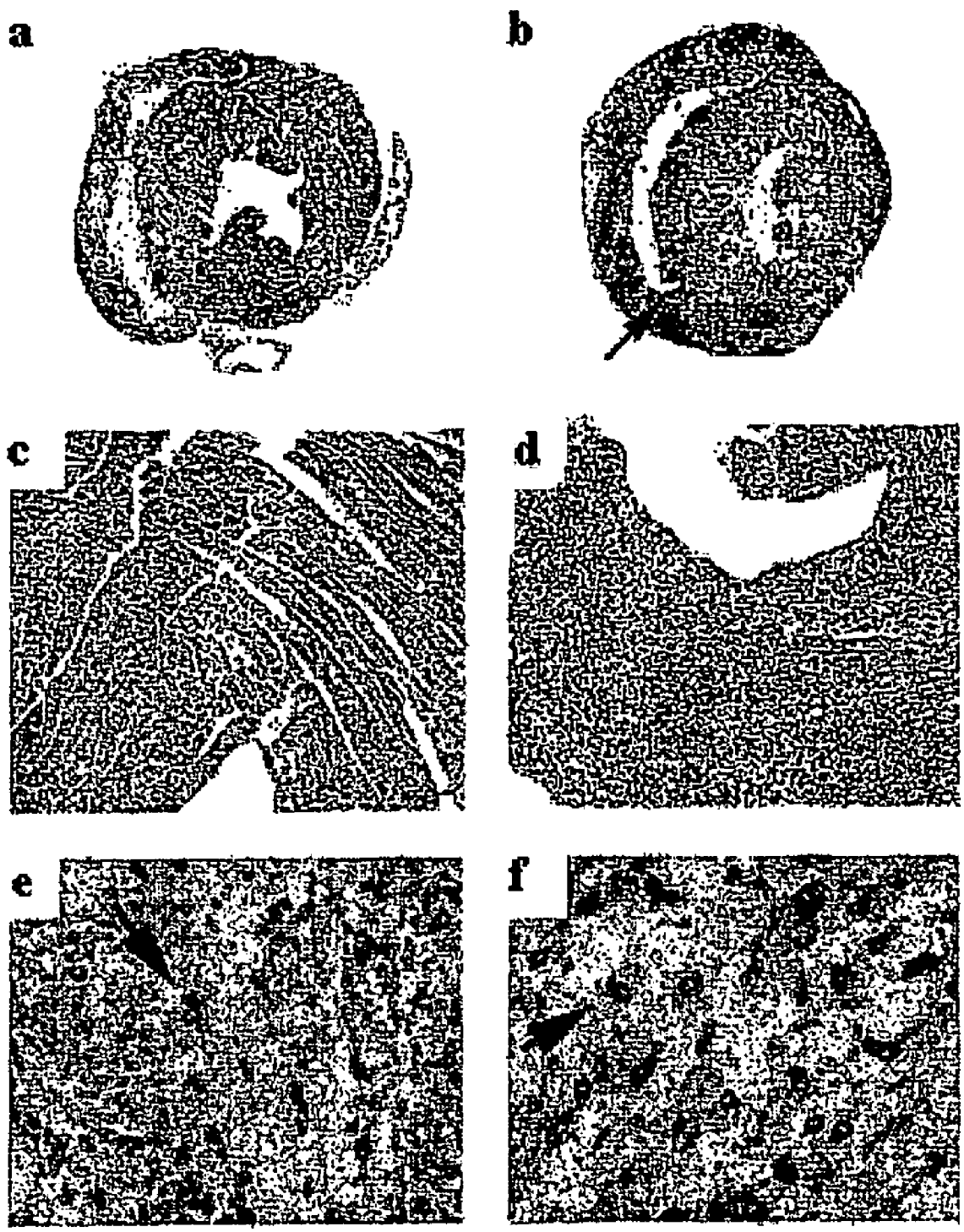
FIG. 1 shows photomicrographs of mouse heart tissue sections at 0× (Panels a and b), 140× (Panels c and d) and 560× (Panels e and f) magnification. Panels 1a and 1c show normal heart tissue while Panels 1b, 1d, 1e and 1f show inflamed heart tissue produced in response to activated dendritic cells pulsed with a portion of the myosin heavy chain α (myhc-α) peptide residues 614 to 629.

In one embodiment, the invention provides a method for stimulating dendritic cells to become reactive to an antigen.

"Dendritic cells", as is known to those skilled in the art, are cells of the immune system which take up and present self antigens and foreign antigens and which form dendrites during maturation.

Dendritic cells may be obtained by various methods described in the scientific literature. Suitable tissue sources include peripheral blood, bone marrow and lymphatic tissues such as spleen or lymph nodes. Dendritic cells may, for example, be obtained by culturing from bone marrow, as described by Lutz et al.[40] or may be isolated directly from suspensions of spleen or lymph node cells by enrichment with magnetic beads specific for dendritic cell surface markers, for example CD11c+.

The majority (~80%) of the dendritic cell population isolated by the method of Lutz et al. from murine bone marrow was found to be CD11c+ CD11b+. The invention is not limited to this subset of dendritic cells and the method of the invention may be applied to any population of dendritic cells from any source. Immature dendritic cells are preferred.

The isolated dendritic cells may, optionally, be further enriched by CD11c+ positive selection, for example using magnetic beads (MACS™, Miltenyi Biotech). Such more purified cell populations may be preferable for human clinical use.

In one embodiment of the invention, isolated dendritic cells are contacted with a selected antigen to which one wishes the cells to become reactive and to at least one Toll-like receptor (TLR) stimulant.

The isolated dendritic cells may be contacted with the selected antigen for a suitable period of time, followed by contacting the dendritic cells with at least one Toll-like receptor (TLR) stimulant for a further period of time.

For an antigen which is a short peptide not requiring processing by the dendritic cells, an antigen exposure time of 30 to 60 minutes is sufficient. For more complex antigens, such as whole proteins or crude cell preparations, antigen exposure should be for about 12 to 24 hours.

Generally, an antigen concentration in the range of 1 to 20 µg/ml is suitable for antigen exposure. High levels of some antibodies may be toxic to dendritic cells, but one of skill in the art can readily determine an optimum antigen concentration or range.

The time period for TLR activation by the TLR stimulant may be from 1 to 4 hours, preferably from about 1 to 2 hours, particularly if high concentrations of TLR stimulant are used, as described herein.

Materials which stimulate or activate members of the TLR family are well known to those skilled in the art and are described in the scientific literature. Any TLR ligand may be used as TLR stimulant to activate dendritic cells in the method of the invention. Suitable TLRs include, for example, lipopolysaccharide (LPS: *E. coli* 0111:B4:Sigma), poly (I:C) (Amersham), CpG-ODN or peptidoglycan (PGN: *S. aureus*: Fluka).

As indicated by the data disclosed herein, activation of dendritic cells by the method of the invention is not limited to stimulation of one particular TLR, since stimulants which stimulate different TLRs have been used successfully.

In a further embodiment of the invention, the dendritic cells are contacted with both a TLR stimulant and an anti-CD40 antibody. Anti-CD40 antibodies may be obtained commercially.

Co-activation of dendritic cells with a TLR stimulant and an anti-CD40 antibody enhanced both the reactivity and the life span of treated cells, compared with activation by TLR stimulant alone. Anti-CD40 antibody concentrations in the range 3 to 5 µg/ml gave good results but concentrations outside that range may also be employed.

Reactive dendritic cells prepared by the above-described method are the foundation of a number of novel methods.

For example, if the selected antigen to which the dendritic cells are exposed is a tumor antigen, the dendritic cells reactive to this antigen may be used in immunotherapy of the tumor from which the antigen was derived.

In accordance with this embodiment, the invention provides a method for treating a tumor in an animal, such as a human, by obtaining a tumor antigen expressed by the tumor, obtaining a sample of dendritic cells from the animal; contacting the dendritic cells with the tumor antigen for a suitable period of time; contacting the dendritic cells with at least one TLR stimulant, and optionally also with an anti-CD40 antibody, for a suitable period of time, as described above; and reintroducing the activated dendritic cells into the animal.

Initially, a biopsy sample is obtained from the tumor to permit identification of one or more antigens expressed by the tumor. The biopsy sample may be screened for known, characterized tumor antigens. If one or more of these are identified, a corresponding synthetic antigenic protein or peptide may be used for contacting the dendritic cells. If no known tumor antigen is identified, a single cell suspension is prepared from the tumor biopsy and the cell suspension is rendered apoptotic by a known method, e.g. irradiation or addition of chemical compounds. The apoptotic cell preparation is used to contact the subject's dendritic cells and expose the cells to tumor antigens.

A sample of dendritic cells is obtained from the tumor-bearing animal, for example from peripheral blood or bone marrow, as described above. Preferably, the dendritic cells are cultured in the presence of a cytokine such as IL-10 to suppress maturation and the cells are contacted in vitro with the synthetic tumor antigen or the apoptotic cell preparation for 12 to 24 hours. The tumor-bearing animal may be a human.

The dendritic cells are washed to remove cytokines, if used, and contacted with at least one TLR stimulant and optionally an anti-CD40 antibody, as described above. The treated cells are washed and reintroduced into the animal bearing the tumor, for example by intravenous infusion or subcutaneous injection. Repeated delivery of cells may be required to maintain the animal's immune response to the tumor. For human immunotherapy, suitable dosages of cells and timing of repeat deliveries can be determined by the treating physician, in accordance with conventional methods of determining suitable dosages.

Tumors which may be treated by the method of the invention include, but are not limited to melanomas, renal cell carcinomas, leukemias and lymphomas.

The method of the invention may also be used to produce animal models of various autoimmune diseases, to assist in understanding the development of these diseases and to provide a screening tool for the assessment of candidate compounds for their ability to stop or interfere with the disease process, providing for identification of potential pharmaceutical compounds for disease treatment.

To create such animal models, dendritic cells obtained from the animal are stimulated to become reactive to an autoantigen associated with the autoimmune disease by the method described herein and are then reintroduced into the animal to allow development of the disease.

To produce an animal model of, for example, autoimmune heart disease, dendritic cells from a non-human animal are contacted with a heart-specific antigen, such as the myhc-α peptide described herein, and a TLR stimulant, in the method of the invention and are then reintroduced into the animal, as described herein, to produce myocarditis.

Similarly, animal models of other diseases, such asthma or arthritis, may be produced. For example, collagen or other structural proteins making up the matrix of joint cartilage may be used as antigen to create an animal model of arthritis, proinsulin as antigen for a model of diabetes, myosin peptides as antigen for a model of autoimmune myocarditis, MOG or other myelin-derived peptides for autoimmune encephalomyelitis and foreign airway antigens for asthma.

Animal models may be created using a variety of mammals, including mice, rats and pigs.

In another embodiment of the present invention there is provided a method for activating dendritic cells to induce organ specific autoimmunity that can be used as a model to study organ failure. The method as described above is used with the modification that the autoantigen used to pulse the dendritic cells is organ specific and after reintroduction of the activated dendritic cells into the animal, results in organ failure. The murine α-myosin-heavy chain peptide (myhc-α$_{614-629}$) [Ac-SLKLMATLFSTYASAD-OH][11,23] (myhc-α) (SEQ ID NO:1) was used as an autoantigen to induce dilated cardiomyopathy and subsequent heart failure. The model system can be used to elucidate mechanisms involved in diseases in which organ failure has an autoimmune component, for example diabetes, arthritis, lupus, etc.

In another embodiment of the present invention there is provided a method for activating dendritic cells and using these cells as an in vitro drug screening assay to identify compounds capable of influencing the development of organ specific autoimmunity. The method as described above is used, for example using an animal model of an autoimmune disease, and further comprises the steps of applying test compounds to the dendritic cells either before pulsing with antigen, during pulsing, after pulsing prior to TLR activation, during TLR activation or after TLR activation. The compounds applied may influence development or progression of autoimmunity in the target organ, either to inhibit or to accelerate. After reintroduction of the activated dendritic cells into the test animal, a determination is made as to whether the compounds applied have influenced the development or progression of autoimmunity in the animal.

It has been shown that inoculation of dendritic cells pulsed with heart muscle specific self-peptide induces CD4$^+$ T-cell mediated autoimmune myocarditis. Dendritic cell mediated heart inflammation progressed and worsened into dilated cardiomyopathy and heart failure even after resolution of acute inflammatory infiltrates. Importantly, dendritic cell mediated autoimmunity and heart disease only occurred when dendritic cells were activated through Toll-like receptors. Moreover, disease pathogenesis depended on CD40 costimulation. Thus, the concerted activation of the innate and adaptive immune system renders dendritic cells autoaggressive.

Autoimmunity and Heart Failure

Immunization with myhc-α pulsed dendritic cells resulted in dilation of the heart chambers, impaired contractility, and caused fibrotic changes after resolution of acute inflammatory infiltrates. These data are in line with the fact that explanted hearts or biopsies of patients with post-infectious cardiomyopathy do not necessarily display inflammatory infiltrates, even in the presence of autoantibodies[5]. Thus, the results mirror the pathogenesis of post-infectious dilated cardiomyopathy in men. Following dendritic cells immunization of mice, autoantibodies were generated against the myhc-α epitope as well as against other myosin epitopes. The question arises whether these autoantibodies contribute or even mediate heart failure after resolution of acute inflammatory infiltrates. For instance, autoantibodies against a surface protein of cardiomyocytes mediate heart failure in BALB/c mice lacking the negative immunoregulatory PD-1 receptor[31]. Alternatively, cardiac dysfunction might reflect the inability of the heart to cope with tissue destruction resulting in pathological remodelling and fibrosis.

Infections and inflammation have emerged as important risk factors for cardiovascular diseases[1], the major cause of death in Western societies. These results indicate that presentation of self-antigen together with stimulation of TLRs on dendritic cells is sufficient to trigger autoimmune heart disease might explain cardiac dysfunction in patients with sepsis[32] and the clinical association between a worse prognosis after myocardial infarction and the magnitude of the systemic inflammatory response[1,2,3,4]. Moreover, autoimmune mechanisms have been suggested in heart failure after infection with the protozoan Trypanozoma cruzii[9]. Our experimental system establishes a novel in vivo disease model to study the pathophysiology of post-inflammatory heart failure and to develop new treatment strategies. Importantly, our data provide a direct causal link between autoimmune heart disease and the development of dilated cardiomyopathy and heart failure.

Innate Immunity, Infections and Autoimmunity

Autoimmune diseases affect up to 10% of the general population. Besides genetic susceptibility, environmental triggers and infectious agents have been implicated in the pathogenesis of multiple autoimmune diseases[7,33]. However, in most autoimmune diseases the causative infectious agents have never been identified and it is not known how different pathogens can break immunotolerance and trigger tissue-specific autoimmunity.

Figure 7:
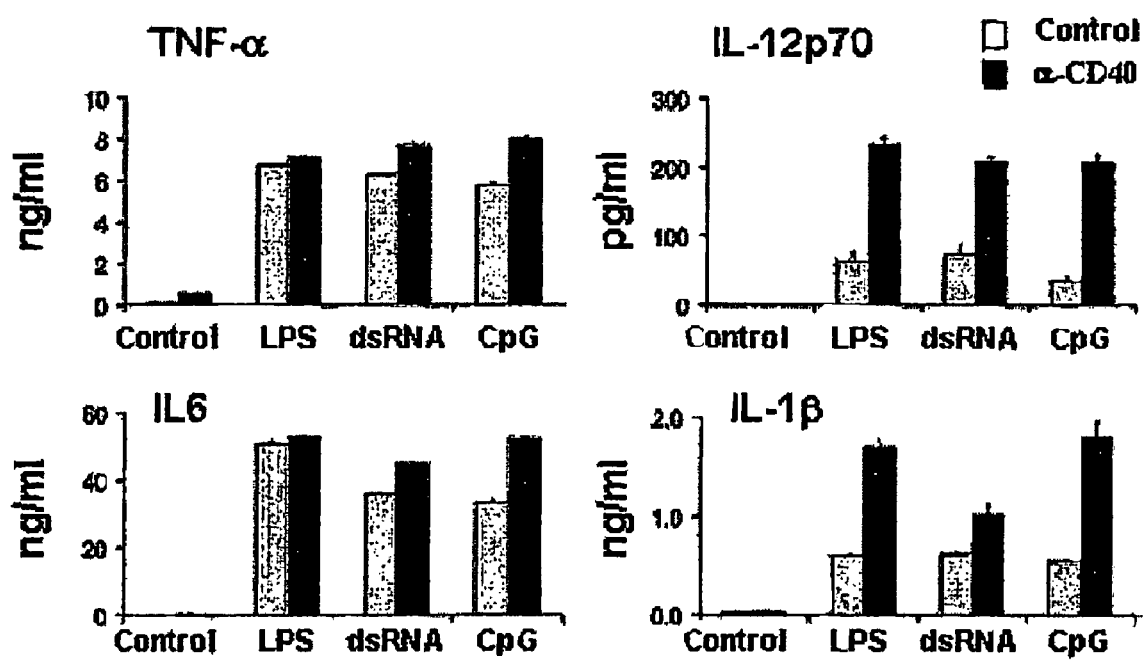
FIG. 7 shows production of the cytokines TNF-α, IL-12p 70, IL6 and IL-1β by dendritic cells stimulated for 12 hours with the indicated Toll-like receptor stimulants (1 µg/ml LPS, 100 µg/ml poly(I:C) (dsRNA) or, 10 µM CpG-ODN), in the absence or presence of the stimulating anti-CD40 antibody (α CD40:5 µg/ml). Data are expressed as mean (±SD) from quadruplicate culture wells and represent one of several experiments with similar data.
Figure 8:
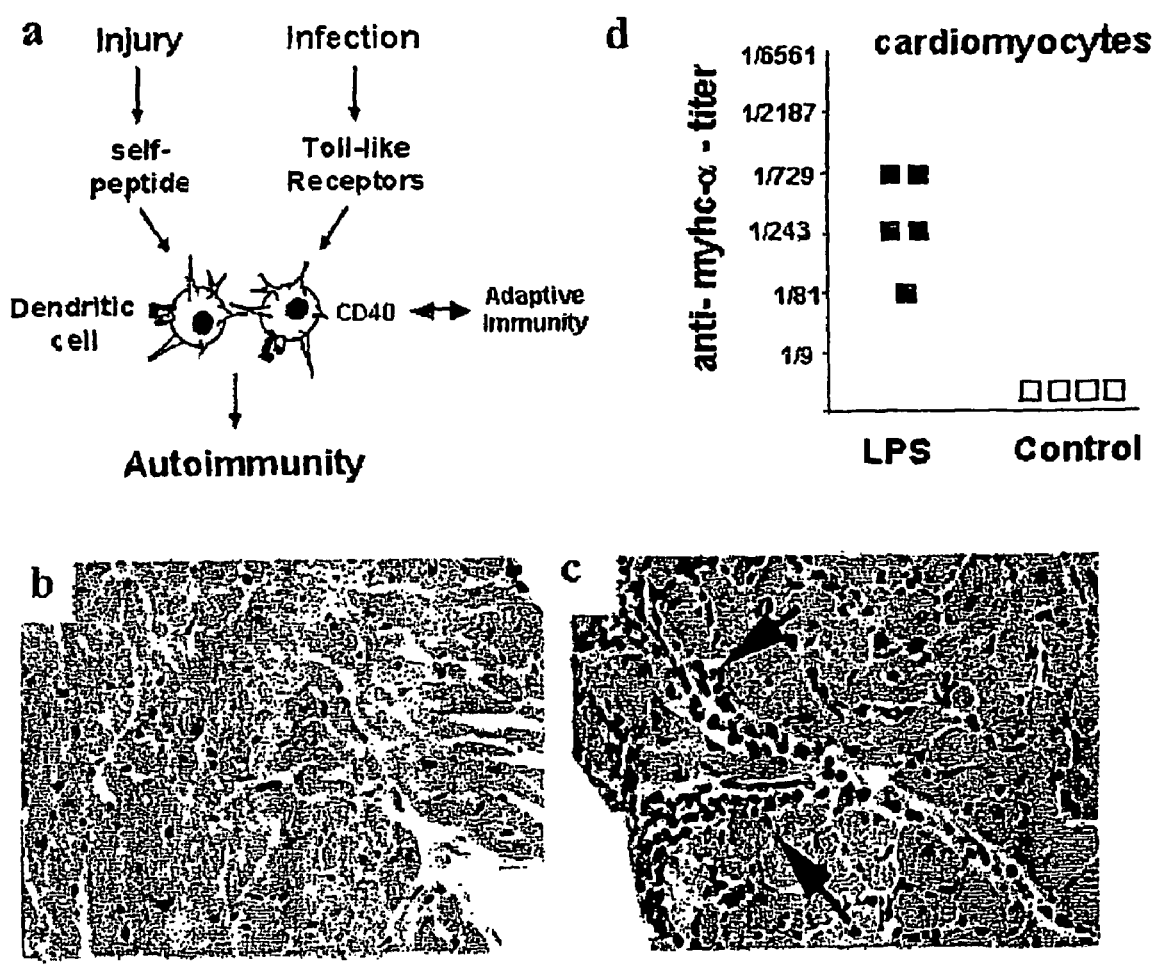
FIG. 8, Panel a, shows in schematic form a proposed model of autoimmune pathogenesis wherein tissue injury releases self-antigens that are captured and presented by dendritic cells. In the event of Toll-like receptor activation, an autoreactive T cell response arises, which is amplified by CD40-CD40L interactions.

These results indicate that activation of TLRs is essential to induce tissue specific autoimmune heart disease provide a molecular framework for the pathogenesis of autoimmunity. In the context of heart damage and microbial infections, self-peptide pulsed dendritic cells might be stimulated by either viral RNA acting through TLR3, whereas bacteria might induce TLR2, 4 and 9 through cell wall products like peptidoglycans, LPS, or unmethylated DNA[21]. Moreover, products from the cardiotropic protozoon T. cruzii have recently been shown to activate TLR2 on dendritic cells[34]. Thus, autoimmunity not necessarily requires antigenic mimicry between microbial antigens and self-proteins[33]. Rather, tissue injury in concert with activation of the innate immune system appears to trigger autoimmunity in genetically susceptible individuals (FIG. 7a). In contrast, uptake of released self-antigen under steady state conditions or in the presence of only minimal dendritic cells stimulation might result in tolerance and downregulation of autoreactive T-cells[17,18,19].

Autoimmunity in humans and in experimental animal models often shows a relapsing disease pattern[7,33]. For instance, patients with dilated cardiomyopathy often show rapid worsening of their cardiac functions following infection of any cause[4]. Intriguingly, in vivo activation of TLRs in mice after resolution of myhc-α induced myocarditis results in a relapse of cardiac infiltrates and rapid worsening of heart functions (U. Eriksson & Josef M. Penninger, unpublished). Therefore, unspecific in vivo stimulation of the innate immune system can rapidly induce tissue specific inflammation in previously primed animals. We therefore propose that exacerbations and relapses in autoimmune diseases might occur in genetically susceptible humans that experience unspecific stimulation of TLRs in vivo.

These results show that dendritic cells can induce rapid onset, organ specific autoimmunity in naïve mice in response to an endogenous antigen. The proposed model of dendritic cell induced myocarditis provides a novel experimental paradigm to induce autoimmunity and heart failure. The ability of autoantigen-pulsed dendritic cells to induce massive autoimmunity needs to be extended to other systems such as asthma or arthritis. The use of the model system will aid in the design and development of novel therapeutic strategies for autoimmune diseases that selectively act on dendritic cells and to optimize tissue specific dendritic cells based cancer vaccination protocols. Since both, dendritic cell mediated autoimmunity and heart disease only occur when dendritic cells are activated through Toll-like receptors, these results provide a unifying theory as to how tissue damage and multiple infectious triggers can induce autoimmune diseases and chronic cardiomyopathy.

EXAMPLES

The examples are described for the purposes of illustration and are not intended to limit the scope of the invention.

Methods of chemistry, molecular biology, protein and peptide biochemistry and immunology referred to but not explicitly described in this disclosure and examples are reported in the scientific literature and are well known to those skilled in the art.

For statistical analysis, dichotomous data were analyzed by Fisher's exact test. The Mann-Whitney U test was used for the evaluation of severity scores. Proliferation responses and cytokine levels were compared using ANOVA and the t-test.

Example 1

Self-Antigen Pulsed, Activated Dendritic Cells Induce Myocarditis

To determine if self-protein pulsed DCs can trigger autoimmunity to endogenous antigens, the previously identified heart muscle specific alpha-myosin peptide, residues 614 to 629[11,23] (myhc-α) was used to inoculate mice. All mice used were either wild-type mice, SCID mice lacking B and T-cells, or IL4Rα$^{-/-}$ mice and all were on BALB/c background and purchased from Jackson Laboratories. Mice were kept under specific pathogen-free conditions. Bone-marrow derived dendritic cells were generated as described in Lutz et al.[40] Fluorescent Activated Cell Sorting (FACS) analysis showed that over 80% of the dendritic cells were CD11c$^+$CD11b$^+$ dendritic cells, which were further enriched by CD11c$^+$ positive selection using magnetic beads (MACS™, Miltenyi Biotech). After overnight pulsing with 10 μg/ml of the murine α-myosin-heavy chain peptide (myhc-α$_{614-629}$) [Ac-SLKL-MATLFSTYASAD-OH][11,23] (SEQ ID NO:1), dendritic cells were activated for 4 hours with a TLR stimulus including either 1 μg/ml LPS (*E. coli* 0111:B4; Sigma), 100 μg/ml poly(I:C) (Amersham), 10 μM CpG-ODN, or 10 μg/ml PGN (*S. aureas*; Fluka), with or without either 5 μg/ml RANK-L (R&D Biosystems). For some experiments dendritic cells were stimulated with 500 U/ml TNF-α or 10 ng/ml of IL-1β (both Pepro Tech) in the presence or absence of anti-CD40 Antibody.

BALB/c (H2$^d$ haplotype) mice were injected with syngeneic, myhc-α pulsed CD11c$^+$ CD11b$^+$ CD80$^+$ CD86$^+$ CD8$^-$ MHC class II$^+$ bone-marrow-derived dendritic cells activated with the TLR-trigger LPS and/or a stimulating anti-CD40 antibody. Mice were i.p. injected with 50,000 to 200,000 dendritic cells/mouse. Control mice received activated dendritic cells pulsed with ova-peptide (OVA). Mice were sacrificed and hearts removed at different time points after the first DC inoculation. Myocarditis was scored using grades from 0 to 4 where 0 indicates no inflammatory infiltrates; 1 means small foci of inflammatory cells between myocytes; 2 means larger foci of more than 100 inflammatory cells; 3 means more than 10% of a cross-section involved; and 4 means more than 30% of a cross-section is involved.

Heart sections from mice 10 days after inoculation of myhc-α or OVA peptide-pulsed LPS/anti-CD40 activated dendritic cells are shown in FIG. 1. Control hearts showing the absence of inflammation in mice immunized with OVA pulsed dendritic cells are shown in FIGS. 1a and 1c. In FIGS. 1b and 1d, massive inflammation after inoculation of myhc-α pulsed dendritic cells is indicated by the arrow. Representative whole heart images and larger magnifications (×140) are shown (H&E staining). For immunohistochemistry on frozen heart sections the following antibodies were used: anti-MHC II (biotinylated, Serotec, MCA46B), anti-CD3 (KT3-1.1), anti-CD4 (YTS 191), anti-CD8 (YTS 169), and anti-CD11c (2.5 mg/ml, clone HL3, Pharmingen). FIGS. 1e and 1f show immunohistochemically stained cross sections illustrating that infiltrates consist of low numbers of CD8$^+$ cells (1e, arrow) and high numbers of CD4$^+$ cells (1f, arrow). Original magnifications ×560.

Neither inoculation of activated dendritic cells pulsed with a non-specific OVA peptide nor inoculation of non-activated, myhc-α pulsed dendritic cells induced inflammation of the heart (FIG. 1a,c, Table 1). Activation of dendritic cells with anti-CD40 antibody alone was also not effective in inducing myocarditis. Moreover, inoculation of myhc-α pulsed dendritic cells activated with LPS and anti-CD40 for 24 hours using previously established maturation protocols[13,14] did not result in heart inflammation (data not shown).

Pulsing of dendritic cells with myhc-α followed by a very short in vitro activation with anti-CD40 and LPS for 4 hours rendered dendritic cells reactive. Inoculation of these dendritic cells induced massive myocarditis in Balb/c mice (FIG. 1b,d, Table 1). The disease onset was very rapid starting 5 days after the dendritic cell immunization and peaking at day 10. Of note, even a single inoculation of myhc-α pulsed dendritic cells induced disease, but at lower prevalence compared to repetitive inoculations. Moreover, myhc-α pulsed dendritic cells activated with LPS alone for 4 hours also induced moderate heart inflammation at lower prevalence (Table 1). These results provide the first experimental evidence that dendritic cells can induce rapid onset organ specific inflammation in naïve mice in response to an endogenous antigen.

TABLE 1

Myhc-α pulsed dendritic cells trigger autoimmune heart disease

| Recipient | Antigen | Activation [in vitro] | Dendritic cell Inoculation (Day) | Prevalence (day 10) | Severity grade at day 10 [median (individual data)] |
|---|---|---|---|---|---|
| Wild type | myhc-α | LPS/α-CD40 | 0, 2, 4 | 10/10*† | 3(1, 2, 2, 3, 3, 3, 3, 4, 4, 4) |
| Wild type | myhc-α | None | 0, 2, 4 | 0/5† | 0 |
| Wild type | OVA | LPS/α-CD40 | 0, 2, 4 | 0/8* | 0 |
| Wild type | myhc-α | LPS/α-CD40 | 0 | 3/6 | 3(0, 0, 0, 3, 3, 3) |
| Wild type | OVA | LPS/α-CD40 | 0 | 0/5 | 0 |
| Wild type | myhc-α | LPS | 0, 2, 4 | 4/7 | 1(0, 0, 0, 1, 1, 2, 2)‡ |
| Wild type | myhc-α | α-CD40 | 0, 2, 4 | 0/5† | 0 |
| Wild type | myhc-α | LPS/RANK-L | 0, 2, 4 | 2/5 | 0(0, 0, 0, 1, 2) |

*P < 0.0001,
†P < 0.0005 (Fisher's Exact Test).
‡P < 0.0028 (Mann-Whitney U Test).

Example 2

Dendritic Cell Immunization Induces Autoimmunity

To determine whether dendritic cells induced myocarditis and fulfilled the criteria for autoimmunity, it was first necessary to determine whether defined self-antigens were present. CD4+ T-cells were purified from spleens of mice immunized with myhc-α pulsed, LPS/anti-CD40 antibody activated dendritic cells using magnetic beads (CD4+ T-cell isolation kit; Miltenyi Biotech GmbH). The CD4+ T-cells were cultured for 40 hours with irradiated (2000 rad) syngeneic splenocytes and either 10 µg/ml myhc-α or ovalbumin in serum-free AIM-V (Gibco) medium. Cytokine levels were measured using commercially available Quantikine ELISA kits (R&D Biosystems, Minneapolis, U.S.A). Alternatively, proliferation was assessed by measuring [$^3$H]methyl-thymidine incorporation after culture for 72 hours. For cytokine measurements, dendritic cells were plated at $1 \times 10^6$/ml in 24-well plates and incubated for 12 hours with various TLR stimuli including 1 µg/ml LPS, 100 µg/ml poly(I:C), 10 µM CpG-ODN, or 10 µg/ml PGN with or without either 5 µg/ml of anti-CD40. Cytokines were measured using Quantikine ELISA kits (R&D Biosystems, Minneapolis). For FACS analysis, dendritic cell preparations were preincubated for 30 min at 4° C. with Fc-block (Pharmingen) and 1% rat serum in Pharmingen staining buffer before staining with the appropriate fluorochrome labeled antibodies from Pharmingen.

Figure 2:
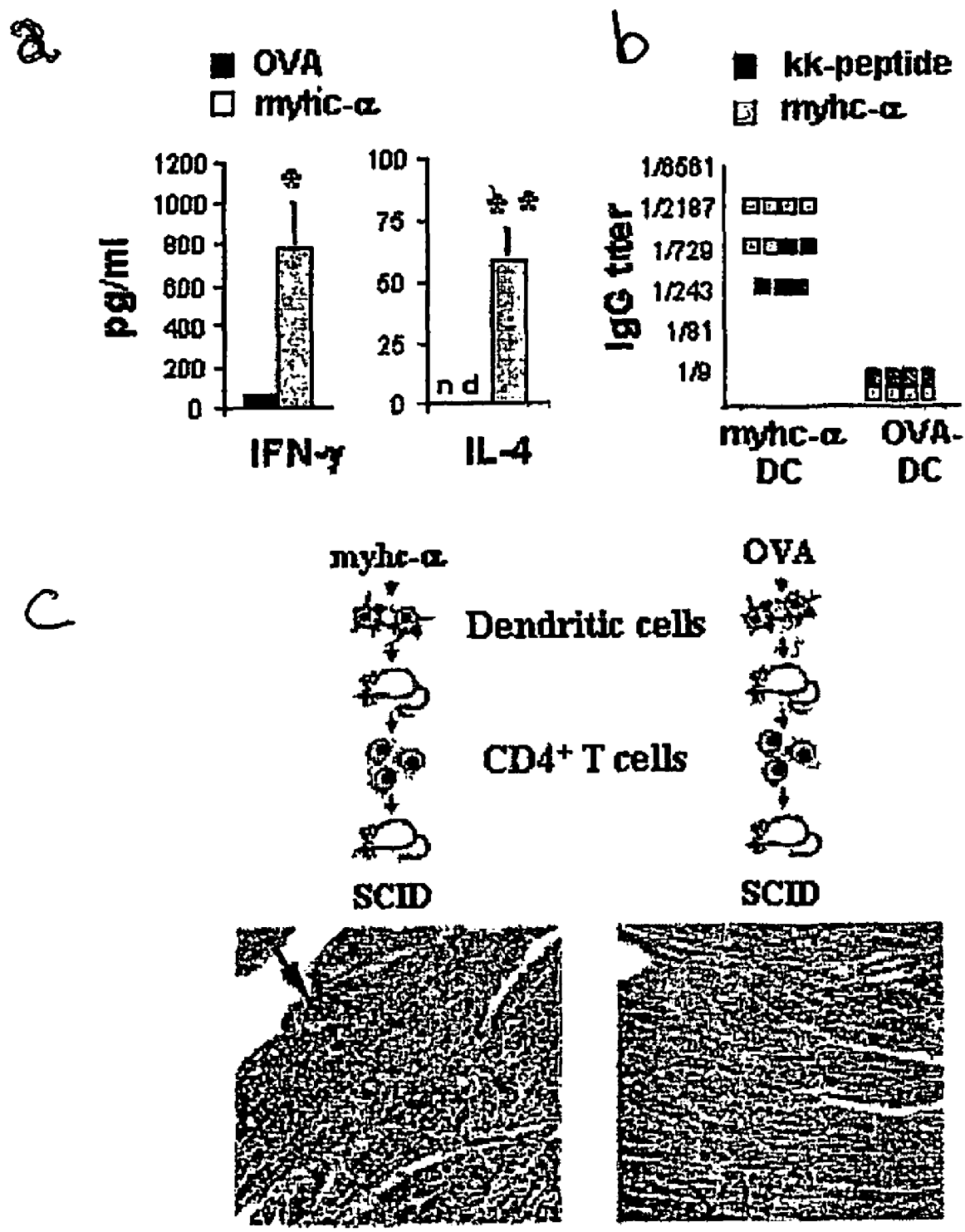
FIG. 2, Panel a, shows IFN-γ and IL-4 production of CD4+ T-cells from mice inoculated with activated dendritic cells pulsed with myhc-α or OVA, expressed as pg/ml; Panel 2b shows in vivo production of auto IgG antibodies in mice inoculated with activated dendritic cells pulsed with either myhc-α or control ova-peptide (OVA); Panel 2c shows sections of cardiac tissue showing myocarditis in SCID mice injected with myhc-α primed CD4+ T cells but not in mice injected with OVA-primed CD4+ T cells.

IFN-γ and IL-4 were measured after 40 hours and the data are shown in FIG. 2a. Values indicate means (±SD) of 5 individual mice where **$p<0.005$ for IL-4, and *$p<0.0001$ (ANOVA and unpaired t-test) for IFN-γ production of CD4+ T-cells isolated from mice injected with myhc-α pulsed dendritic cells compared to mice injected with OVA pulsed dendritic cells (n.d.=not detectable).

Dendritic cell-induced myocarditis was antigen-specific, because dendritic cells pulsed with non-relevant antigen did not induce disease (Table 1). Furthermore, there were no infiltrates in other organs such as skeletal muscle, lungs, or kidneys (not shown), indicating that dendritic cell-induced inflammation was organ-specific and limited to the heart. Immunohistochemistry revealed that most of the T-cells infiltrating the hearts of diseased animals were CD4+ and only a few cells were positive for CD8+ (FIG. 1e,f). In vitro restimulation of CD4+ T-cells purified from DC-injected mice with myhc-α resulted in proliferation (not shown) and IFN-γ and IL-4 production (FIG. 2a). In contrast, CD4+ T-cells restimulated with non-specific OVA peptide did not proliferate and produced no IL-4 and only low amounts of IFN-γ. These data show that dendritic cells prime myhc-α-specific CD4+ T-cells in vivo.

To determine whether dendritic cell-induced myocarditis fulfilled the criteria for autoimmunity, it was necessary to determine whether autoantibodies that can transfer disease were present. Antibody responses against the heart specific myhc-α and kk peptides were assessed by ELISA as described[11], using HRP-labeled goat anti-mouse IgG antibodies (Southern Biotechnology Associates). Titers were determined at half maximum $OD_{405\ nm}$. Anti-myhc-α and anti-kk IgG autoantibodies were detected 10 days after inoculation of activated, myhc-α pulsed dendritic cells, but not after OVA pulsed dendritic cells. Titers from individual mice are shown in FIG. 2b.

Dendritic cell-induced myocarditis was accompanied by a strong IgG autoantibody response against the heart specific myhc-α peptide (FIG. 2b). Also detected were autoantibodies against a heart specific peptide, termed kk[25], that was independent of the immunizing myhc-α peptide (FIG. 2b), confirming that dendritic cells are capable of inducing heart inflammation and this event is accompanied by the generation of autoantibodies to endogenous heart peptides. Importantly, in vitro restimulation and transfer of myhc-α primed, but not OVA-primed, CD4+ T-cells into syngeneic, immunodeficient SCID mice resulted in myocarditis of the host animals (FIG. 2c). In contrast, transfer of CD8+ T cells did not induce disease (not shown). Moreover, inoculation of IFN-γR$^{-/-}$ and IL-4Rα$^{-/-}$ mice with myhc-α-pulsed wild-type dendritic cells resulted in strong myocarditis in both strains (Table 1). Thus, disease induction by dendritic cells appears to be independent from Th1/Th2 polarisation. Thus, this model of dendritic cells-induced myocarditis fulfils all criteria for CD4+ T-cell mediated autoimmune diseases and provides a novel experimental paradigm to induce autoimmunity.

CD4+ and CD8+ T-cells were isolated from spleens of mice immunized with myhc-α pulsed and activated dendritic cells using magnetic beads (MACS™, Miltenyi Biotech). After 48 hours of culture of myhc-α pulsed, irradiated (1500 Rad) syngenic DC in the presence of 5 µg/ml of anti-CD28 mAb (Pharmingen), $1 \times 10^7$ CD4+ T-cells per mouse (>98% CD4+- cells) were transferred i.p. into SCID (BALB/c) recipient mice. All recipients were sacrificed 10 days later. No myocarditis was observed in SCID mice (n=5) after transfer of CD4+ T-cells isolated from mice immunized with OVA pulsed dendritic cells. $p<0.05$, Fisher's exact test.

Example 3

Immunization with Myhc-α Pulsed, Activated Dendritic Cells Results in Contractile Dysfunction and Dilated Cardiomyopathy A causal link between dilated cardiomyopathy and post-infectious autoimmune myocarditis has never been established. In the mouse model of the present invention, inflammation peaked 5 to 10 days after dendritic cell-inoculation and started to resolve around day 12 after the last dendritic cell-inoculation (results not shown). It was important to determine whether dendritic cell-induced myocarditis would progress to cardiomyopathy after resolution of the inflammatory infiltrates.

Echocardiographic assessments were carried out as described[41]. Isoflurane-anesthetized mice were examined by transthoracic echocardiography using a 12-MHz probe (Hewlett Packard). Ejection velocity, left ventricular end-systolic (LVESD), and end-diastolic (LVEDD) dimensions were recorded and a percentage fractional shortening (FS) calculated according to the following formula: FS (%)= (LVEDD-LVESD)/LVEDD. VCFC was calculated as FS/ejection time corrected for heart rate.

Figure 3:
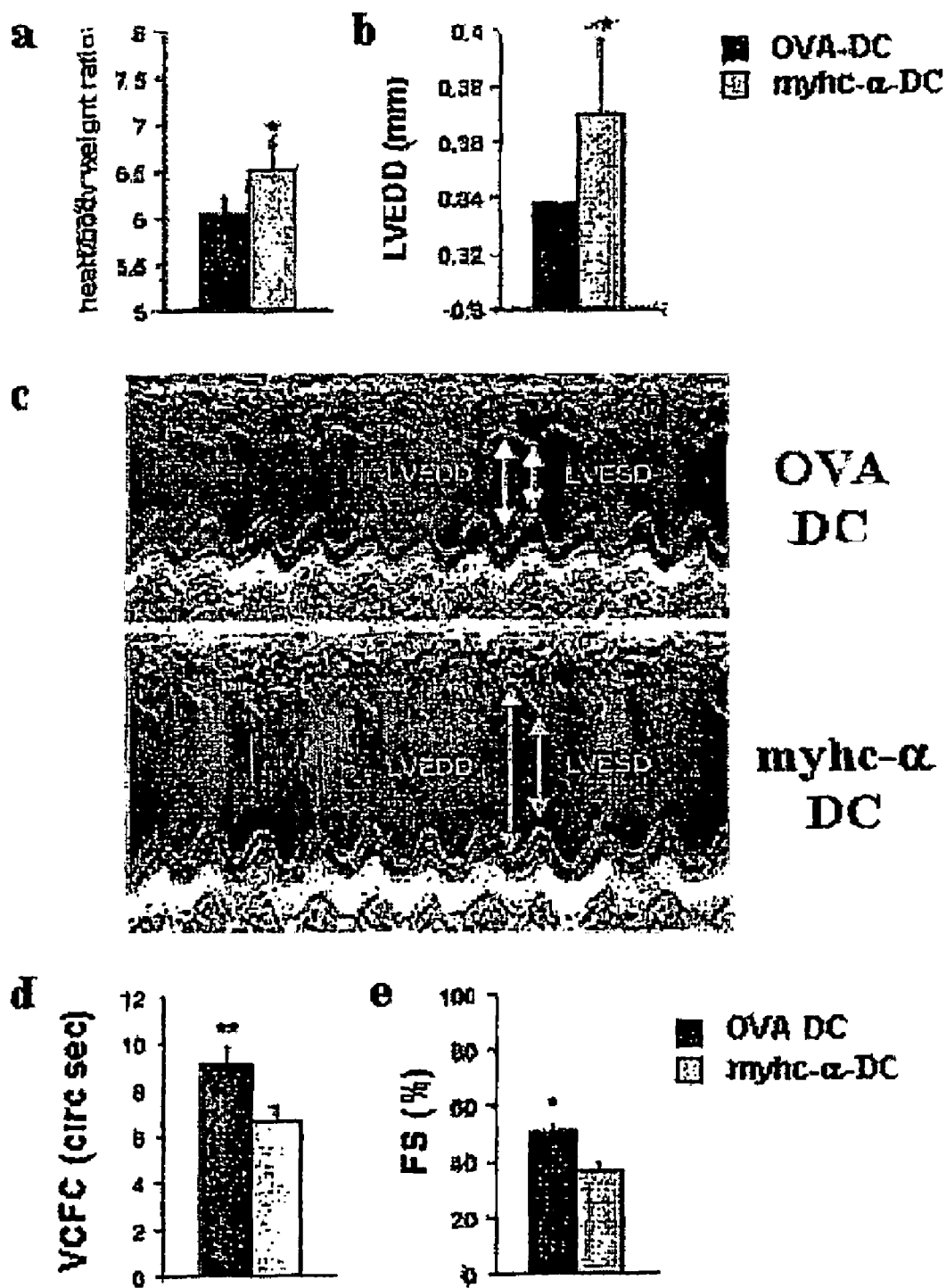
FIG. 3 shows data that indicate contractile dysfunction and onset of dilated cardiomyopathy in mice inoculated with activated dc's pulsed with myhc-α.

FIG. 3a shows heart/body weight ratios (mg/g) and echocardiography data of hearts from mice injected with activated myhc-α pulsed dendritic cells compared to controls injected with OVA pulsed dendritic cells 4 weeks after immunization. Mean values ±SD are shown. Heart/body weight ratios where n=8 per group and *$p<0.005$. FIG. 3b shows increased left ventricular end-diastolic diameters (LVEDD) in mice injected with myhc-α pulsed dendritic cells where n=8 per group and $p<0.05$. FIG. 3c shows representative echocardiograms from a myhc-α pulsed dendritic cells immunized mouse and a control animal immunized with OVA pulsed dendritic cells. Arrows indicate the distance between systolic contraction (LVESD) and diastolic relaxation (LVEDD). Note the massive enlargement of the heart dimension in the myhc-α dendritic cells immunized animal indicative of dilated cardiomyopathy. FIG. 3d shows a decrease in velocity of circumferential fiber shortening (VCFC) (n=5, p<0.05) while FIG. 3e shows decrease in fractional shorting (% FS) (n=8, *p<0.005) in myhc-α pulsed dendritic cells immunized mice as functional readouts for impaired contractility.

In contrast to control animals injected with OVA-pulsed dendritic cells, heart/body weight ratios progressively increased in mice injected with myhc-α pulsed dendritic cells (FIG. 3a). These enlarged hearts lacked inflammatory infiltrates but displayed interstitial fibrosis (not shown), which is often seen in heart failure. Intriguingly, echocardiography of mice 4 weeks after dendritic cells immunization showed increased left ventricular end diastolic (LVEDD) and left ventricular end systolic (LVESD) dimensions indicative of dilated cardiomyopathy (FIG. 3b,c). Furthermore, mice immunized with myhc-α pulsed dendritic cells developed severe cardiac dysfunction as determined by impaired velocity of circumferential fiber shortening (VCFC) (FIG. 3d) and decreased fractional shortening (FS) (FIG. 3e). Thus, immunization with myhc-α pulsed dendritic cells results in fibrotic changes, dilation of the heart chambers, and impaired contractility. These data provide a direct causal link between autoimmune heart disease and the development of dilated cardiomyopathy and heart failure.

Example 4

Role of CD40 in Dendritic Cell-Mediated Autoimmunity

Activation of dendritic cells via CD154-CD40[26,27], 4-1BB-4-1BB-L[28], or RANK-RANK-L[29] ligand-receptor interactions are critical for dendritic cell maturation and the expression of costimulatory molecules and cytokine production. It was necessary to determine which one of these molecular interactions was involved in the ability of injected dendritic cells to initiate an "autoaggressive" response.

For in vivo CD40-CD40L blocking, 200 μg of the anti-CD40L blocking antibody (MR-1) was injected[30] into mice. 4-1BBL-4-1BB interactions were blocked using the TKS-1 monoclonal antibody [200 μg] as described[28]. Controls received a non-specific isotype antibody (Pharmingen). RANK-RANKL interactions were blocked in vivo using a human OPG fusion protein at 250 μg/mouse[39]. All blocking agents were i.p. injected in 200 μl PBS/mouse every second day.

Addition of recombinant RANK-L to myhc-α pulsed dendritic cell cultures during LPS activation did not enhance myocarditis susceptibility beyond that observed with LPS alone (Table 1). Furthermore, in vivo blockade of RANK-RANK-L interactions by the decoy receptor OPG had no apparent effect on the severity or incidence of dendritic cell mediated disease (Table 2 and data not shown). Similar to RANKL-RANK, inhibition of 4-1BB in in vitro dendritic cells cultures (not shown) or in vivo using the blocking TSK-1-antibody[28] (not shown) had no evident influence on disease incidence or disease severity.

Figure 4:
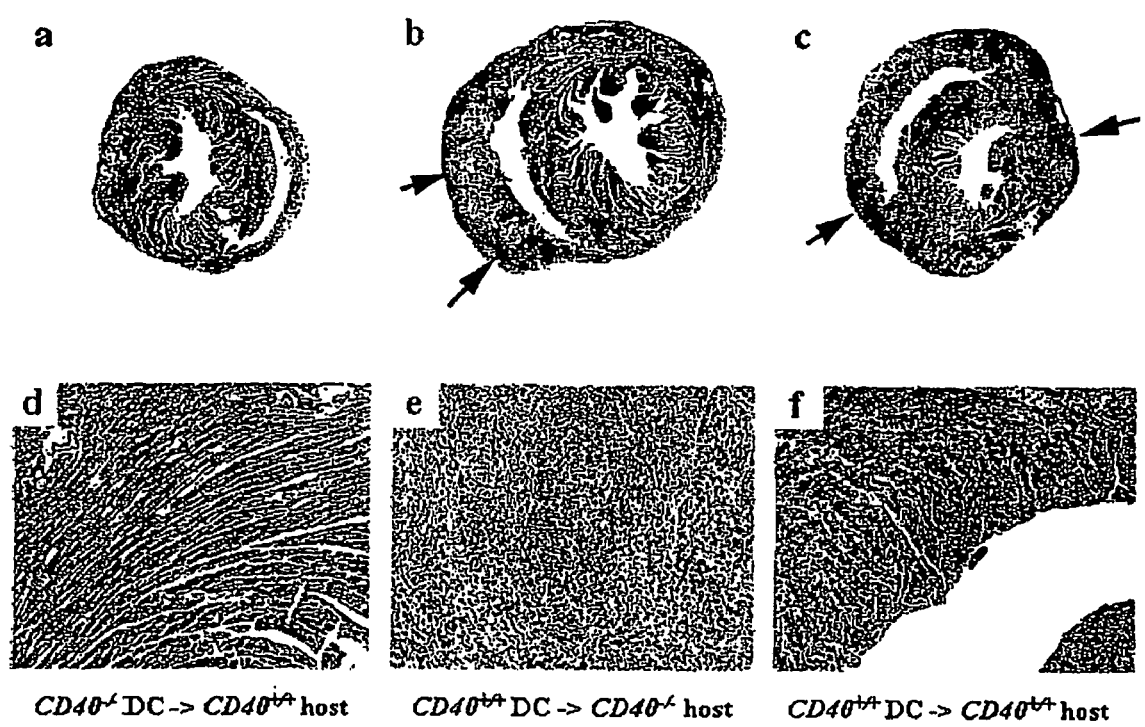
FIG. 4 shows mouse heart tissue in cross section at 0× and 140× magnification after inoculation with activated dc's pulsed with myhc-α.

In contrast, in vitro costimulation of myhc-α dendritic cells with LPS and a stimulating anti-CD40 antibody markedly enhanced dendritic cell-induced heart inflammation (Table 1). Given that activated dendritic cells interact in vivo with T-cells expressing CD40L, we treated dendritic cell-inoculated mice with a CD40L blocking antibody[30]. In vivo blocking of CD40-CD40L interactions almost completely prevented disease (Table 2). The role of CD40 costimulation was then genetically confirmed by the fact that myhc-α pulsed CD40$^{-/-}$ dendritic cells did not induce myocarditis in CD40$^{+/+}$ mice (Table 2, FIG. 4a,d). FIGS. 4a and 4d indicate the absence of heart inflammation in heart tissue after inoculation of CD40$^{-/-}$ dendritic cells into wild type recipient mice. Importantly, inoculation of CD40$^{+/+}$ dendritic cells into CD40$^{-/-}$ (FIG. 4b,e) triggered heart inflammation to a similar extent as in wild type recipients (FIG. 4c,f and Table 2). FIGS. 4b and 4e indicate cardiac inflammation (arrows) after inoculation of wild type dendritic cells into CD40$^{-/-}$ recipients. FIGS. 4c and 4f indicate inflammatory infiltrates in both ventricles (arrows) after inoculation of wild-type dendritic cells into wild type recipients. Representative whole heart images and larger magnifications (×140) are shown. H&E staining. Data are from mice 10 days after inoculation of myhc-α pulsed LPS/anti-CD40 treated dendritic cells.

TABLE 2

Selective requirement for CD40 in dendritic cell-mediated cardiac inflammation

| Activation [in vitro] | Recipients | Dendritic cell genotype | Treatment (in vivo) | Prevalence (day 10) | Severity grade at day 10 [median (individual data)] |
|---|---|---|---|---|---|
| LPS/α-CD40 | Wild-type | Wild-type | Sham | 7/7* | 3(2, 2, 3, 3, 3, 4, 4) |
| LPS/α-CD40 | Wild-type | Wild-type | OPG-Fc | 7/7 | 3(1, 2, 3, 3, 4, 4, 4) |
| LPS/α-CD40 | Wild-type | Wild-type | Anti-CD40L | 3/8* | 0(0, 0, 0, 0, 0, 11, 1, 2) |
| LPS/α-CD40 | Wild-type | CD40$^{-/-}$ | None | 1/7† | 0(0, 0, 0, 0, 0, 0, 1) |
| LPS/α-CD40 | CD40$^{-/-}$ | Wild-type | none | 5/5† | 3(2, 2, 3, 3, 4) |

*P < 0.0256,
†P < 0.0152 (Fisher's exact test).

Example 5

TLR Stimulation Renders Dendritic Cells Autoaggressive

Although CD40 stimulation was found to be important for the development of autoimmune heart disease, heart inflammation could only be initiated when we co-activated dendritic cells with LPS that stimulates Toll-like receptor 4 (TLR 4). Moreover, myhc-α pulsed dendritic cells activated with LPS alone could induce moderate heart inflammation at low prevalence (Table 1). Diverse classes of pathogens have been implicated in the pathogenesis of autoimmunity and different infectious triggers can activate the innate immune system via distinct TLRs[21]. We therefore examined whether this effect was specific to LPS or whether activation of other TLRs was also sufficient to induce dendritic cell-mediated autoimmunity.

Figure 5:
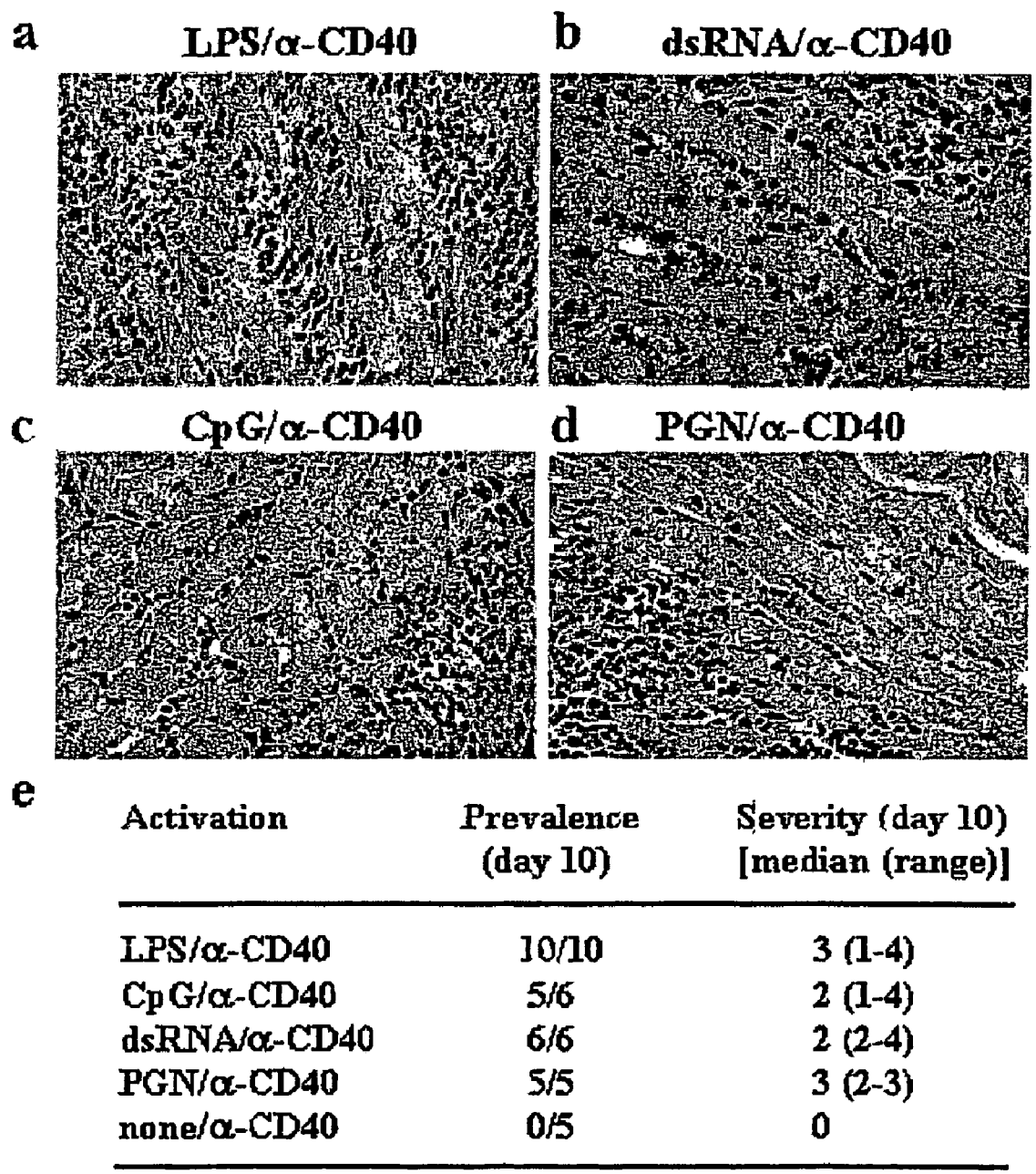
FIG. 5 shows mouse heart tissue in cross section at 560× magnification 10 days after inoculation of myhc-α pulsed dc's activated with (Panel a) LPS/anti-CD40; (Panel b) dsRNA/anti-CD40; (Panel c) CpG/anti-CD40; and (Panel d) PGN/anti-CD40.

Stimulation of myhc-α pulsed dendritic cells with LPS (TLR 4) or peptidoglycan (which stimulates TLR 1, TLR 2 and TLR 6) or dsRNA (which stimulates TLR 3), or CpGs (that stimulate TLR 9)[ref.21] resulted in severe myocarditis (FIG. 5a-e). Heart sections from mice 10 days after inoculation of myhc-α-pulsed dendritic cells are shown in FIGS. 5a to 5d (magnification ×560) when activated with: LPS/anti-CD40 (FIG. 5a); dsRNA/anti-CD40 (FIG. 5b); CpG/anti-CD40 (FIG. 5c); and PGN/anti-CD40 (FIG. 5d). Disease prevalence and severity of inflammation in individual mice is shown in FIG. 5, bottom panel. Representative heart images (H&E staining) are shown.

Inflammatory infiltrates consisted of mononuclear cells, mainly macrophages and CD4+ T-cells, granulocytes and some eosinophils. For all TLR tested, disease induction depended on CD4+ T cells using adoptive transfer experiments (not shown). Thus, TLRs can provide a common signal to render dendritic cells "autoaggressive". These findings show that three molecular events must coincide for dendritic cell mediated autoimmune myocarditis to occur: uptake of self-protein in a genetically susceptible background, specific costimulation by the host's immune system via CD40, and most importantly, activation of TLRs. Intriguingly, stimulation of all tested TLRs on dendritic cells was sufficient to initiate an autoaggressive response.

Example 6

CD40 and TLR Cooperate in IL-16 and IL-12 Production by Dendritic Cells

FIGS. 6a and 6b show the expression of costimulatory molecules on CD40+/+ (6a) and CD40−/− (6b) dendritic cells after stimulation with LPS/anti-CD40 for 12 hours. FACS histograms were gated on CD11c+ CD11b+ MHC class II+ live cells (ICAM, B7.1, B7.2) or CD11c+ CD11b+ live cells. The disease promoting effect of CD40 co-stimulation does not appear to be due to enhanced expression of co-stimulatory molecules.

Figure 6C:
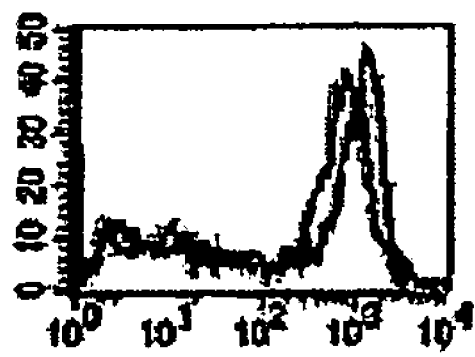
Figure 6C:
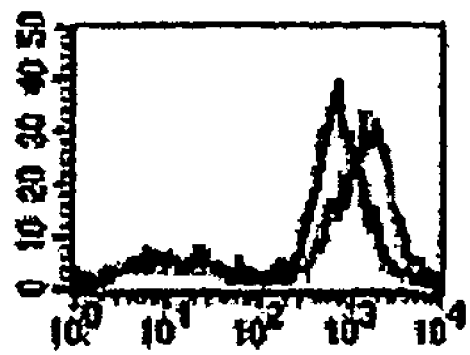
Figure 6C:
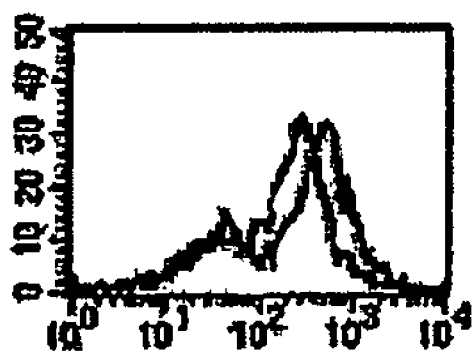
Figure 6C:
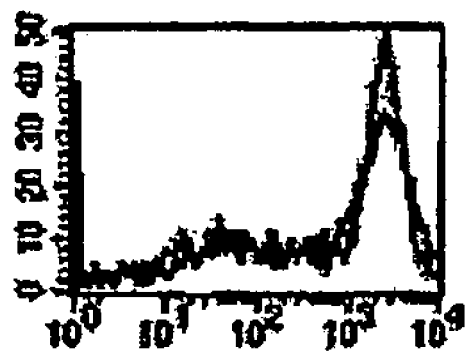

As shown In FIG. 6c, the upregulation of activation markers like MHC class II molecules, CD80, CD86, and ICAM-1 did not differ after stimulation of CD40+/+ or CD40−/− dendritic cells with anti-CD40 plus LPS. Furthermore, there were no observable differences in TNF-α or IL-6 production after stimulation of wild-type dendritic cells with various TLR stimuli in the absence or presence of CD40 activation (FIG. 6c). FIG. 6c shows levels of cytokine production in dendritic cells that were stimulated for 12 hours with the indicated TLR stimulants (1 µg/ml LPS, 100 µg/ml poly(I:C), 10 µM CpG-ODN, or 10 µg/ml PGN) in the absence or presence of the stimulating anti-CD40 antibody (5 µg/ml). Data are expressed as mean (±SD) from quadruplicate culture wells and represent one of several experiments with similar data.

In contrast, IL-1β and IL-12p70 levels significantly differed between dendritic cells stimulated through CD40 or TLR only and those activated with TLR stimuli plus anti-CD40 as shown in FIG. 6c. These differences were not due to variations in dendritic cells apoptosis up to 24 hours of in vitro culture (not shown). Thus, CD40 and TLR stimulation co-operate in the induction of the cytokines IL-1β and IL-12p70 in dendritic cells.

To address whether IL-1β and IL-12p70 were important for dendritic cell mediated inflammatory heart disease, we immunized IL-1R1 and IL-12β1-receptor-mutant mice with peptide-pulsed, anti-CD40 and TLR-activated dendritic cells. In all cases, both signalling through the IL-1 receptor type 1 and the IL12-IL12R system were found to be required to trigger autoimmunity (Table 3). However, inoculation of wild-type dendritic cells induced myocarditis and autoaggressive CD4+ T-cells in IL-1R1−/− mice, but not in IL-12Rβ1−/− mice. In contrast, wild-type recipients developed myocarditis after inoculation of IL-12Rβ1−/− dendritic cells, but not after inoculation of IL-1R1−/− dendritic cells (Table 3). Thus, induction of CD4+ T-cell mediated myocarditis requires IL-1R1 signalling on dendritic cells but not on CD4+ T-cells. In contrast, IL-12 signalling on activated, antigen-pulsed dendritic cells is not essential for the capacity of these cells to trigger autoimmunity. Rather, IL-12 receptor signalling is critical on CD4+ effector T-cells because adoptive transfer of in vitro restimulated IL-12Rβ1−/− CD4+ T-cells isolated from IL-12Rβ1+/+ dendritic cell immunized IL-12Rβ1−/− mice does not induce disease in syngeneic SCID mice (not shown). The novel experimental system of the present invention for the first time makes it possible to selectively dissect the essential functions of cytokines and/or costimulatory molecules on dendritic cells versus effector cells in an autoimmune disease model in vivo.

TABLE 3

Role of IL-12 and IL-1 signaling in dendritic cell induced heart disease

| Recipients | Dendritic cell genotype | Dendritic cell Inoculations | Prevalence (day 10) | Severity grade at day 10 [median (individual data)] |
|---|---|---|---|---|
| Wild-type | Wild-type | Day 0, 2, 4 | 6/6* | 2(2, 2, 2, 2, 3, 3) |
| IL-12Rβ1−/− | Wild-type | Day 0, 2, 4 | 1/8*† | 0(0, 0, 0, 0, 0, 0, 0, 1) |
| Wild-type | IL-12Rβ−/− | Day 0, 2, 4 | 6/8† | 2(0, 0, 2, 2, 2, 3, 2, 3) |
| IL-1R1−/− | Wild-type | Day 0, 2, 4 | 5/5‡ | 2(1, 2, 2, 3, 2) |
| Wild-type | IL-1R1−/− | Day 0, 2, 4 | 0/5‡ | 0 |

*P < 0.005,
†P < 0.05,
‡P < 0.01 (Fisher's Exact Test).

Example 7

Tissue Injury Together with Activation of the Innate Immune System is Sufficient to Induce Cardiac Inflammation In Vivo Other than genetic susceptibility, environmental and infectious triggers have been implicated in the pathogenesis of multiple autoimmune diseases in animal models and humans[7,33]. However, no such infectious triggers have yet been definitively identified and the mechanisms whereby different pathogens could trigger autoimmunity have never been clarified. The results described above indicate that stimulation of self-antigen-pulsed DCs via CD40 and TLR renders these antigen-presenting cells autoaggressive. Since activation of all tested TLR was sufficient for the development of dendritic cell-induced autoimmune heart disease, and without being bound to a theory, it is hypothesized that tissue injury in conjunction with an unspecific inflammatory trigger should result in autoimmunity in vivo. In the proposed model of autoimmune pathogenesis illustrated schematically in FIG. 7a, tissue injury releases self-antigens that are captured and presented by dendritic cells. In the event of Toll-like receptor activation, an autoreactive T-cell response arises, which is amplified by CD40-CD40L interactions.

To test this hypothesis, mice were injected with various numbers of apoptotic cardiomyocytes purified from adult mice together with/or without 100 µg/mouse anti-CD40 and 10 µg LPS/mouse on three consecutive days. Cardiomyocyte apoptosis was induced either by irradiation with UVA (10 J/m$^2$) or by adding 10 µmol/l $H_2O_2$ to culture wells.

Apoptotic cardiomyocytes where then injected into syngeneic Balb/c mice followed by in vivo stimulation of TLRs. Inoculation of 2×10$^6$ apoptotic cardiomyocytes (i.p.) by themselves without LPS did not result in any disease (0 of 6 mice) as shown in FIG. 7b. However, i.p. inoculation of only 2×10$^6$ apoptotic cardiomyocytes, followed by in vivo activation of TLR 4 with LPS, resulted in inflammatory foci in the hearts as shown in FIG. 7c. Inoculation of 2×10$^6$ apoptotic cardiomyocytes (i.p.) together with LPS (10 µg i.p. on day 0,1,2) resulted in cardiac inflammation (arrows in FIG. 7c) in 7 out of 8 mice. Of note, inoculation of LPS alone did not induce heart inflammation (0 of 5 mice; not shown) at p<0.0001 for LPS and cardiomyocytes compared to just cardiomyocytes (Fisher's exact test). Moreover, i.p. inoculation of both UV-irradiated or $H_2O_2$ treated cardiomyocytes followed by in vivo activation of TLR 4 with LPS was sufficient to induce cardiac inflammation. Importantly, this heart inflammation was accompanied by the generation of IgG autoantibodies against the cardiac specific myhc-α peptide as shown in FIG. 7d. FIG. 7d shows anti-myhc-α IgG autoantibody titers 10 days after i.p. inoculation of LPS and 2×10$^6$ apoptotic cardiomyocytes (LPS). Inoculation of cardiomyocytes alone did not induce relevant antibody titers (Control). Data from individual mice are shown. In contrast, control inoculations of apoptotic cardiomyocytes in the absence of TLR activation did not induce cardiac autoantibodies. It should be noted that in vivo LPS or CpG inoculations, or CD40 plus LPS inoculations alone did not result in myocarditis (not shown). These results show that systemic release of damaged cardiomyocytes in combination with unspecific activation of the innate immune system is sufficient to induce cardiac inflammation.

The present invention is not limited to the features of the embodiments described herein, but includes all variations and modifications within the scope of the claims.

REFERENCES

1. Libby, P., Ridker, P. M., & Maseri, A. Inflammation and atherosclerosis. Circulation. 105, 1135-1143 (2002).
2. Liuzzo, G., et al. The prognostic value of C-reactive protein and serum amyloid A protein in severe unstable angina. N. Engl. J. Med. 331, 417-424 (1994).
3. Roig, E., et al. Serum interleukin-6 in congestive heart failure secondary to idiopathic dilated cardiomyopathy. Am. J. Cardiol. 82, 688-690, A8 (1998).
4. Mann, D. L. Inflammatory mediators and the failing heart: past, present, and the foreseeable future. Circ. Res. 91, 988-998 (2002).
5. Calabrese, F., et al. Molecular diagnosis of myocarditis and dilated cardiomyopathy in children: clinicopathologic features and prognostic implications. Diagn. Mol. Pathol. 11, 212-221 (2002).
6. Caforio, A. L., Mahon, N. J., Tona, F., & McKenna, W. J. Circulating cardiac autoantibodies in dilated cardiomyopathy and myocarditis: pathogenetic and clinical significance. Eur. J. Heart Fail. 4, 411-417 (2002).
7. Rose, N. R., Herskowitz, A., Neumann, D. A., & Neu, N. Autoimmune myocarditis: a paradigm of post-infection autoimmune disease. Immunol. Today. 9,117-120 (1988).
8. Feldman, A. M., & McNamara, D. Myocarditis. N. Engl. J. Med. 343,1388-1398 (2000).
9. Pontes-de-Carvalho, L., et al. Experimental chronic Chagas' disease myocarditis is an autoimmune disease preventable by induction of immunological tolerance to myocardial antigens. J. Autoimmun. 18,131-138 (2002).
10. Neu, N., et al. Cardiac myosin induces myocarditis in genetically predisposed mice. J. Immunol. 139, 3630-3636 (1987).
11. Bachmaier, K., et al. Chlamydia infections and heart disease linked through antigenic mimicry. Science 283, 1335-1339 (1999).
12. Smith, S. C., & Allen, P. M. Expression of myosin-class II major histocompatibility complexes in the normal myocardium occurs before induction of autoimmune myocarditis. Proc. Natl. Acad. Sci. U.S.A. 89, 9131-9135 (1992).
13. Banchereau, J., & Steinman, R. M. Dendritic cells and the control of immunity. Nature 392, 245-252 (1998).
14. Mellman, I., & Steinman, R. M. Dendritic cells: specialized and regulated antigen processing machines. Cell 106, 255-258 (2001).
15. Pulendran, B., Palucka, K., & Banchereau, J. Sensing pathogens and tuning immune responses. Science 293, 253-256 (2001).
16. Steinman, R. M., & Nussenzweig, M. C. Avoiding horror autotoxicus: the importance of dendritic cells in peripheral T cell tolerance. Proc. Natl. Acad. Sci. U.S.A. 99, 351-358 (2001).
17. Turley, S. J. Dendritic cells: inciting and inhibiting autoimmunity. Curr. Opin. Immunol. 14, 765-770 (2002).
18. Liu, K., et al. Immune tolerance after delivery of dying cells to dendritic cells in situ. J. Exp. Med. 196, 1091-1097 (2002).
19. Menges, M., S. et al. Repetitive inoculations of dendritic cells matured with tumor necrosis factor alpha induce antigen-specific protection of mice from autoimmunity J. Exp. Med. 195,15-21 (2002).
20. Ludewig, B., Odermatt, B., Landmann, S., Hengartner, H., & Zinkemagel, R. M. Dendritic cells induce autoimmune diabetes and maintain disease via de novo formation of local lymphoid tissue. J. Exp. Med. 188, 1493-1501 (1998).
21. Medzhitov, R. & Janeway, C. A. Jr. Decoding the patterns of self and nonself by the innate immune system. Science 296, 298-300 (2002).
22. Means, T. K., et al. Human Toll-Like Receptors Mediate Cellular Activation by *Mycobacterium tuberculosis* J. Immunol. 163, 3920-3927 (1999).
23. Pummerer, C. L., et al. Identification of cardiac myosin peptides capable of inducing autoimmune myocarditis in BALB/c mice J. Clin. Invest. 97, 2057-2062. (1996).
24. Rose, N. R. & Bona, C. Defining criteria for autoimmune diseases (Witebskys postulates revisited). Immunol. Today. 14, 426-430 (1993).

25. Donermeyer, D. L., Beisel, K .W., Allen, P. M., & Smith, S. C. Myocarditis-inducing epitope of myosin binds constitutively and stably to I-Ak on antigen-presenting cells in the heart. J. Exp. Med. 182,1291-300 (1995).
26. Grewal, I. S., J. Xu, & Flavell, R. A. Impairment of antigen-specific T-cell priming in mice lacking CD40 ligand. Nature 378, 617-620 (1995).
27. Cella, M., et al. Ligation of CD40 on dendritic cells triggers production of high levels of interleukin-12 and enhances T cell stimulatory capacity: T-T help via APC activation. J. Exp. Med. 184, 747-752 (1996).
28. Futagawa, T. et al. Expression and function of 4-1BB and 4-1BB ligand on murine dendritic cells. Int. Immunol. 14, 275-286 (2002).
29. Josien, R., et al. TRANCE, a Tumor Necrosis Factor Family Member, Enhances the Longevity and Adjuvant Properties of Dendritic Cells In Vivo. J. Exp. Med. 191, 495-502 (2000).
30. Howard, L. M., & Miller, S. D. Autoimmune intervention by CD154 blockade prevents T cell retention and effector function in the target organ. J. Immunol. 166,1547-1553 (2001).
31. Nishimura, H., et al. Autoimmune dilated cardiomyopathy in PD-1 receptor-deficient mice. Science. 291,319-322 (2001).
32. Krishnagopalan, S., Kumar, A., Parillo, J. E., & Kumar A. Myocardial dysfunction in the patient with sepsis. Cum Opin. Crit. Care. 8, 376-388 (2002)
33. Benoist, C. & Mathis, D. Autoimmunity provoked by infection: How good is the case for T-cell epitope mimickry? Nat. Immunol. 2, 797-801 (2001).
34. Campos, M. A., et al. Activation of Toll-like receptor-2 by glycosylphosphatidylinositol anchors from a protozoan parasite. J. Immunol. 167, 416-423 (2001).
35. Kawabe, T., et al. The immune responses in CD40-deficient mice: impaired immunoglobulin class switching and germinal center formation. Immunity 1,167-178 (1994).
36. Magram, J., et al. IL-12-deficient mice are defective in IFNγ production and type 1 cytokine responses. Immunity 4, 471-4781 (1996).
37. Labow, M. et al. Absence of IL-1 signaling and reduced inflammatory response in IL-1 type I receptor-deficient mice. J. lmmunol. 159, 2452-2461 (1997).
38. Eriksson, U., Kurrer, M. O., Sebald, W., Brombacher, F., & Kopf, M. Dual role of the IL-12/IFN-gamma axis in the development of autoimmune myocarditis: induction by IL-12 and protection by IFN-gamma. J. Immunol. 167, 5464-5469 (2001).
39. Kong, Y. Y. et al. Activated T cells regulate bone loss and joint destruction in adjuvant arthritis through osteoprotegerin ligand. Nature 402, 304-309 (1999).
40. Lutz, M. B., et al. An advanced culture method for generating large quantities of highly pure dendritic cells from mouse bone marrow. J. Immunol. Methods. 223, 77-92 (1999).
41. Crackower, M. A., et al. Angiotensin-converting enzyme 2 is an essential regulator of heart function. Nature. 417, 822-828 (2002).

What is claimed is:

1. A method for making CD11c+ dendritic cells reactive to an antigen comprising:
    obtaining a sample of CD11c+ dendritic cells; and
    contacting the CD11c+ dendritic cells with at least one antigen, a CD40 stimulant, and at least one Toll-like receptor (TLR) stimulant, wherein the CD11c+ dendritic cells are contacted with the TLR stimulant for up to four hours.
2. The method of claim 1 wherein the CD11c+ dendritic cells are contacted with the antigen and then with the at least one TLR stimulant.
3. The method of claim 1, further comprising obtaining the CD11c+ dendritic cells from peripheral blood, bone marrow, spleen, and/or lymph node of an animal.
4. The method of claim 1, wherein the TLR stimulant is a lipopolysaccharide, a poly (I:C), a CpG-ODN, or a peptidoglycan.
5. The method of claim 1, wherein the CD11c+ dendritic cells are contacted with the antigen for about 30 minutes to about 24 hours.
6. The method of claim 1, wherein the CD11c+ dendritic cells are contacted with the TLR stimulant for up to two hours.
7. The method of claim 1, wherein the CD11c+ dendritic cells are CD11c+ CD11b+ dendritic cells.
8. The method of claim 1, wherein the CD11c+ dendritic cells are contacted with antigen at a concentration of about 1 to 20 g/ml.
9. The method of claim 1, wherein the CD40 stimulant is an anti-CD40 antibody.
10. The method of claim 9, wherein the anti-CD40 antibody is at a concentration of about 3 to 5 g/ml.
11. The method of claim 1, wherein the antigen is an autoantigen or a tumor antigen.

12. A method for treating a tumor in an animal comprising:
obtaining a tumor antigen expressed by the tumor;
obtaining CD11c+ dendritic cells from the animal;
making the CD11c+ dendritic cells reactive to the tumor antigen by the method of claim 1; and
reintroducing the reactive dendritic cells in the animal.

13. The method of claim 12, wherein the animal is a human.

14. The method of claim 12, further comprising reintroducing the dendritic cells into the animal by intravenous infusion or by subcutaneous injection.

15. The method of claim 12, further comprising culturing the dendritic cells with a cytokine prior to contacting them with the antigen.

16. The method of claim 15, wherein the cytokine is IL-10.

17. The method of claim 12, wherein the tumor is a melanoma, a renal cell carcinoma, a leukemia, or a lymphoma.

18. A method of making an animal model of an autoimmune disease comprising:
obtaining an antigen associated with the autoimmune disease;
obtaining a sample of CD11c+ dendritic cells from a non-human animal;
making the CD11c+ dendritic cells reactive to the antigen associated with the autoimmune disease by the method of claim 1; and
reintroducing the reactive dendritic cells into the animal.

19. The method of claim 18, wherein the antigen is collagen or a cartilage matrix protein and the autoimmune disease is arthritis.

20. The method of claim 18, wherein the antigen is a heart-specific antigen and the autoimmune disease is myocarditis.

21. The method of claim 20, wherein the antigen is myhc-peptide.

22. The method of claim 18, wherein the animal is a mouse, a rat, or a pig.

23. A method of making an animal model of organ failure comprising:
obtaining an organ-specific autoantigen;
obtaining a sample of CD11c+ dendritic cells from a non-human animal;
making the CD11c+ dendritic cells reactive to the autoantigen by the method of claim 1; and
reintroducing the reactive dendritic cells into the animal.

24. The method of claim 23, wherein the antigen is myhc-peptide.

25. An animal model of an autoimmune disease made by the model of claim 18.

26. A method for screening a candidate compound for its ability to modulate the development of an autoimmune disease in an animal comprising:
obtaining an autoantigen associated with the autoimmune disease;
obtaining a sample of CD11c+ dendritic cells from a non-human animal;
making the CD11c+ dendritic cells reactive to the autoantigen by the method of claim 1;
reintroducing the reactive dendritic cells into the animal; and
comparing an autoimmune reaction in the animal with an autoimmune reaction in an animal treated with dendritic cells made reactive to the same autoantigen and not exposed to the compound;
wherein the CD11c+ dendritic cells are contacted with the candidate compound prior to contact with the autoantigen, during contact with the autoantigen, after contact with the autoantigen, prior to contact with the TLR stimulant, during contact with the TLR stimulant, or after contact with the TLR stimulant.

27. An antigen-reactive CD11c+ dendritic cell obtained by the method of claim 1.

* * * * *

UNITED STATES PATENT AND TRADEMARK OFFICE
CERTIFICATE OF CORRECTION

PATENT NO.         : 8,124,067 B2                           Page 1 of 1
APPLICATION NO.    : 10/567167
DATED              : February 28, 2012
INVENTOR(S)        : Josef Penninger et al.

It is certified that error appears in the above-identified patent and that said Letters Patent is hereby corrected as shown below:

In title page, item (73) Assignee, delete
"IMBA-Institute Fur Molekulre Biotechnologie GmbH" and insert
--IMBA-Institut für Molekulare Biotechnologie GmbH-- therefor.

Signed and Sealed this
Twenty-sixth Day of June, 2012

David J. Kappos
*Director of the United States Patent and Trademark Office*

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Ser Leu Lys Leu Met Ala Thr Leu Phe Ser Thr Tyr Ala Ser Ala Asp
 1               5                  10                  15
```